US008231040B2

(12) United States Patent
Zemlok et al.

(10) Patent No.: US 8,231,040 B2
(45) Date of Patent: Jul. 31, 2012

(54) VARIABLE COMPRESSION SURGICAL FASTENER CARTRIDGE

(75) Inventors: Michael A. Zemlok, Prospect, CT (US); Frank J. Viola, Sandy Hook, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 44 days.

(21) Appl. No.: 12/417,688

(22) Filed: Apr. 3, 2009

(65) Prior Publication Data

US 2009/0255975 A1 Oct. 15, 2009

Related U.S. Application Data

(60) Provisional application No. 61/044,682, filed on Apr. 14, 2008, provisional application No. 61/044,664, filed on Apr. 14, 2008.

(51) Int. Cl.
*A61B 17/072* (2006.01)
*A61B 17/068* (2006.01)

(52) U.S. Cl. .......... 227/178.1; 227/175.1; 227/901; 227/902; 606/219; 411/457; 411/470

(58) Field of Classification Search .......... 227/901, 227/902, 175.1, 178.1; 606/219; 411/457, 411/470
See application file for complete search history.

(56) References Cited

U.S. PATENT DOCUMENTS

| 1,756,670 | A | 4/1930 | Treat |
| 3,258,012 | A | 6/1966 | Nakayama et al. |
| 3,744,495 | A * | 7/1973 | Johnson .......... 606/142 |
| 3,771,526 | A | 11/1973 | Rudie |
| 3,837,555 | A | 9/1974 | Green |
| 4,014,492 | A | 3/1977 | Rothfuss |
| 4,278,091 | A | 7/1981 | Borzone |
| 4,319,576 | A | 3/1982 | Rothfuss |
| 4,454,875 | A * | 6/1984 | Pratt et al. .......... 606/75 |
| 4,475,679 | A | 10/1984 | Fleury, Jr. |
| 4,527,437 | A | 7/1985 | Wells |

(Continued)

FOREIGN PATENT DOCUMENTS

EP 0 129 442 12/1984

(Continued)

OTHER PUBLICATIONS

European Search Report mailed Oct. 19, 2009 in EP Application No. 09251240.9 filed May 1, 2009.

(Continued)

*Primary Examiner* — Paul R. Durand
*Assistant Examiner* — Michelle Lopez

(57) ABSTRACT

A surgical fastener applying apparatus comprising a cartridge body including a plurality of fastener retention slots arranged in a plurality of rows including at least an inner row and an outer row, a plurality of surgical fasteners disposed in inner and outer rows and configured such that a plurality of fasteners disposed in the inner row have a backspan that has a greater height than a backspan of a plurality of surgical fasteners disposed in the outer row, and an anvil having an inner row and an outer row of depressions for forming the fasteners. A plurality of pushers are operably associated with the plurality of surgical fasteners and configured to eject the surgical fasteners toward a respective depression in an anvil for formation thereof such that upon formation, the plurality of surgical fasteners ejected from the inner row provide a greater compressive force to tissue than the plurality of surgical fasteners ejected from the outer row.

28 Claims, 13 Drawing Sheets

U.S. PATENT DOCUMENTS

| | | | |
|---|---|---|---|
| 4,531,522 A | 7/1985 | Bedi et al. | |
| 4,532,927 A | 8/1985 | Miksza, Jr. | |
| 4,548,202 A | 10/1985 | Duncan | |
| 4,570,623 A * | 2/1986 | Ellison et al. | 606/75 |
| 4,573,469 A * | 3/1986 | Golden et al. | 606/220 |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,627,437 A | 12/1986 | Bedi et al. | |
| 4,741,336 A | 5/1988 | Failla et al. | |
| 4,767,044 A | 8/1988 | Green | |
| 4,809,695 A | 3/1989 | Gwathmey et al. | |
| 4,848,637 A | 7/1989 | Pruitt | |
| 4,881,545 A | 11/1989 | Isaacs et al. | |
| 4,930,503 A | 6/1990 | Pruitt | |
| 4,941,623 A | 7/1990 | Pruitt | |
| 4,978,049 A * | 12/1990 | Green | 227/178.1 |
| 5,027,834 A | 7/1991 | Pruitt | |
| 5,108,422 A | 4/1992 | Green et al. | |
| 5,180,092 A | 1/1993 | Crainich | |
| 5,201,746 A | 4/1993 | Shichman | |
| 5,209,756 A | 5/1993 | Seedhom et al. | |
| 5,219,353 A | 6/1993 | Garvey, III et al. | |
| 5,240,163 A | 8/1993 | Stein et al. | |
| 5,246,443 A * | 9/1993 | Mai | 606/78 |
| 5,282,829 A | 2/1994 | Hermes | |
| 5,342,396 A | 8/1994 | Cook | |
| 5,350,400 A | 9/1994 | Esposito et al. | |
| 5,352,229 A | 10/1994 | Goble et al. | |
| 5,425,489 A | 6/1995 | Shichman et al. | |
| 5,439,479 A | 8/1995 | Shichman et al. | |
| 5,441,193 A | 8/1995 | Gravener | |
| 5,452,836 A | 9/1995 | Huitema et al. | |
| 5,452,837 A | 9/1995 | Williamson, IV et al. | |
| 5,470,010 A | 11/1995 | Rothfuss et al. | |
| 5,478,354 A * | 12/1995 | Tovey et al. | 606/219 |
| 5,484,095 A | 1/1996 | Green et al. | |
| 5,497,931 A | 3/1996 | Nakamura | |
| 5,497,933 A * | 3/1996 | DeFonzo et al. | 227/175.1 |
| 5,501,693 A | 3/1996 | Gravener | |
| 5,509,920 A | 4/1996 | Phillips et al. | |
| 5,571,116 A | 11/1996 | Bolanos | |
| 5,571,285 A | 11/1996 | Chow et al. | |
| 5,584,856 A | 12/1996 | Jameel et al. | |
| 5,620,452 A | 4/1997 | Yoon | |
| 5,634,926 A | 6/1997 | Jobe | |
| 5,667,526 A | 9/1997 | Levin | |
| 5,667,527 A | 9/1997 | Cook | |
| 5,676,674 A | 10/1997 | Bolanos et al. | |
| 5,697,542 A | 12/1997 | Knodel et al. | |
| 5,709,680 A | 1/1998 | Yates et al. | |
| 5,738,474 A * | 4/1998 | Blewett | 411/473 |
| 5,741,268 A | 4/1998 | Schutz | |
| 5,810,822 A | 9/1998 | Mortier | |
| 5,865,361 A | 2/1999 | Milliman et al. | |
| 5,871,135 A | 2/1999 | Williamson, IV et al. | |
| 5,879,371 A | 3/1999 | Gardiner et al. | |
| 5,915,616 A | 6/1999 | Viola et al. | |
| 5,961,521 A | 10/1999 | Roger | |
| 5,964,394 A | 10/1999 | Robertson | |
| 6,083,242 A | 7/2000 | Cook | |
| 6,202,914 B1 | 3/2001 | Geiste et al. | |
| 6,273,897 B1 | 8/2001 | Dalessandro et al. | |
| 6,325,810 B1 | 12/2001 | Hamilton et al. | |
| 6,348,054 B1 | 2/2002 | Allen | |
| 6,706,057 B1 | 3/2004 | Bidoia et al. | |
| 6,786,382 B1 | 9/2004 | Hoffman | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,001,411 B1 | 2/2006 | Dean | |
| 7,044,352 B2 | 5/2006 | Shelton, IV et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,303,106 B2 * | 12/2007 | Milliman et al. | 227/175.1 |
| 7,377,928 B2 | 5/2008 | Zubik et al. | |
| 7,398,908 B2 | 7/2008 | Holsten et al. | |
| 7,401,721 B2 * | 7/2008 | Holsten et al. | 227/176.1 |
| 7,407,075 B2 * | 8/2008 | Holsten et al. | 227/175.1 |
| 7,407,076 B2 | 8/2008 | Racenet et al. | |
| 7,455,676 B2 | 11/2008 | Holsten et al. | |
| 7,481,349 B2 * | 1/2009 | Holsten et al. | 227/176.1 |
| D586,915 S * | 2/2009 | Grim | D24/145 |
| 7,500,979 B2 | 3/2009 | Hueil et al. | |
| 7,547,312 B2 | 6/2009 | Bauman et al. | |
| 7,588,174 B2 * | 9/2009 | Holsten et al. | 227/176.1 |
| 7,641,091 B2 | 1/2010 | Olson et al. | |
| 7,708,180 B2 * | 5/2010 | Murray et al. | 227/175.1 |
| 7,726,538 B2 * | 6/2010 | Holsten et al. | 227/176.1 |
| 7,726,539 B2 * | 6/2010 | Holsten et al. | 227/179.1 |
| 7,735,703 B2 * | 6/2010 | Morgan et al. | 227/176.1 |
| 7,794,475 B2 | 9/2010 | Hess et al. | |
| 7,905,902 B2 * | 3/2011 | Huitema et al. | 606/220 |
| 2002/0042621 A1 | 4/2002 | Liddicoat et al. | |
| 2004/0004105 A1 | 1/2004 | Jankowski | |
| 2004/0073222 A1 | 4/2004 | Koseki | |
| 2004/0167572 A1 * | 8/2004 | Roth et al. | 606/219 |
| 2004/0232195 A1 | 11/2004 | Shelton et al. | |
| 2004/0232199 A1 | 11/2004 | Shelton et al. | |
| 2004/0247415 A1 | 12/2004 | Mangone, Jr. | |
| 2005/0006430 A1 | 1/2005 | Wales | |
| 2005/0006431 A1 | 1/2005 | Shelton et al. | |
| 2005/0006434 A1 | 1/2005 | Wales | |
| 2005/0023324 A1 | 2/2005 | Doll et al. | |
| 2005/0023325 A1 | 2/2005 | Gresham et al. | |
| 2005/0070925 A1 | 3/2005 | Shelton, IV et al. | |
| 2005/0070958 A1 | 3/2005 | Swayze et al. | |
| 2005/0173490 A1 | 8/2005 | Shelton, IV | |
| 2005/0178813 A1 | 8/2005 | Swayze et al. | |
| 2005/0187576 A1 | 8/2005 | Whitman et al. | |
| 2005/0263562 A1 | 12/2005 | Shelton, IV et al. | |
| 2005/0267530 A1 | 12/2005 | Cummins | |
| 2006/0000868 A1 | 1/2006 | Shelton, IV et al. | |
| 2006/0015144 A1 | 1/2006 | Burbank et al. | |
| 2006/0022014 A1 | 2/2006 | Shelton, IV et al. | |
| 2006/0022015 A1 | 2/2006 | Shelton, IV et al. | |
| 2006/0025809 A1 | 2/2006 | Shelton, IV | |
| 2006/0025810 A1 | 2/2006 | Shelton, IV | |
| 2006/0025811 A1 | 2/2006 | Shelton, IV | |
| 2006/0025812 A1 | 2/2006 | Shelton, IV | |
| 2006/0025813 A1 | 2/2006 | Shelton, IV et al. | |
| 2006/0025816 A1 | 2/2006 | Shelton, IV | |
| 2006/0025817 A1 | 2/2006 | Ortiz et al. | |
| 2006/0039779 A1 | 2/2006 | Ringl | |
| 2006/0049230 A1 | 3/2006 | Shelton, IV et al. | |
| 2006/0085030 A1 | 4/2006 | Bettuchi et al. | |
| 2006/0097026 A1 | 5/2006 | Shelton, IV | |
| 2006/0124688 A1 * | 6/2006 | Racenet et al. | 227/175.1 |
| 2006/0163312 A1 | 7/2006 | Viola et al. | |
| 2006/0226196 A1 | 10/2006 | Hueil et al. | |
| 2006/0291981 A1 | 12/2006 | Viola et al. | |
| 2007/0010838 A1 | 1/2007 | Shelton, IV et al. | |
| 2007/0131732 A1 | 6/2007 | Holsten et al. | |
| 2007/0262116 A1 | 11/2007 | Hueil et al. | |
| 2008/0078800 A1 | 4/2008 | Hess | |
| 2008/0078804 A1 | 4/2008 | Shelton et al. | |
| 2009/0255978 A1 * | 10/2009 | Viola et al. | 227/180.1 |

FOREIGN PATENT DOCUMENTS

| | | |
|---|---|---|
| EP | 0 169 044 | 1/1986 |
| EP | 0588081 A | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1 607 048 A1 | 12/2005 |
| EP | 1 785 098 | 8/2006 |
| EP | 1728473 A | 12/2006 |
| EP | 1 754 445 A2 | 2/2007 |
| EP | 1 875 868 | 1/2008 |

| | | |
|---|---|---|
| EP | 1 917 918 | 5/2008 |
| EP | 2 095 777 | 9/2009 |
| EP | 2 095 777 A2 | 9/2009 |
| FR | 2838952 | 10/2003 |
| GB | 2019296 A | 10/1979 |
| GB | 2 029 754 | 3/1980 |
| GB | 2029754 A | 3/1980 |
| GB | 2051287 A | 1/1981 |
| SU | 405234 | 9/1975 |
| SU | 1333319 | 8/1987 |
| SU | 1442191 | 12/1988 |
| SU | 1459659 | 2/1989 |
| WO | WO 86/02254 A1 | 4/1986 |
| WO | WO 90/05489 | 5/1990 |
| WO | WO 96/19146 | 6/1996 |
| WO | WO 97/34533 | 9/1997 |
| WO | WO 02/30296 A | 4/2002 |
| WO | WO 03/094743 | 11/2003 |
| WO | WO 03/094747 | 11/2003 |
| WO | WO 2006/055385 A | 5/2006 |
| WO | WO 2008/007377 | 1/2008 |
| WO | WO2008/039250 | 4/2008 |
| WO | WO2008/089050 | 7/2008 |

OTHER PUBLICATIONS

European Search Report for EP 06016963.8-2318 date of completion is Mar. 9, 2007.
European Search Report mailed Nov. 16, 2009 in European Patent Application No. EP 09 251 793.7, filed Jul. 15, 2009.
International Search Report from EP Application No. 07 25 4366 dated Nov. 11, 2010.
International Search Report from EP Application No. 09 25 1067 mailed Mar. 17, 2011.
European Search Report EP08 25 2283 dated Jan. 15, 2009.
European Search Report EP09 25 1224.3-2310 dated Oct. 8, 2009.
European Search Report EP09251268 dated Sep. 25, 2009.
European Search Report EP10251797 dated Jan. 31, 2011.
European Search Report EP11004299.1269 dated Aug. 12, 2011.

* cited by examiner

VARIABLE COMPRESSION SURGICAL FASTENER CARTRIDGE

CROSS-REFERENCE TO RELATED APPLICATIONS

This application claims priority to U.S. Provisional Application Ser. Nos. 61/044,682 and 61/044,664 each filed on Apr. 14, 2008, the contents of which are incorporated herein by reference in their entirety.

BACKGROUND

1. Technical Field

The present disclosure relates to surgical fastener applying apparatus. More particularly, the present disclosure relates to a surgical fastener cartridge that includes a plurality of surgical fasteners configured to apply varying compressive forces to tissue, and methods of using the same.

2. Background of the Related Art

Many varieties of surgical fastening apparatus are known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. U.S. Pat. Nos. 5,915,616, 6,202,914, 5,865,361, and 5,964,394 each describe one or more suitable apparatus which may be employed while performing one of these procedures.

In general, a surgical fastening apparatus will include an anvil that is approximated relative to a fastener cartridge during use or a fastener cartridge that is approximated relative to an anvil. The anvil includes depressions that are aligned with, and/or are in registration with slots defined in the cartridge, through which the fasteners will emerge, to effectuate formation. The fastener cartridge typically has one or more rows of fasteners disposed laterally or radially of a channel or knife slot that is configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

Various types of surgical fasteners are well known in the art, including but not limited to unitary fasteners and two-part fasteners. Unitary fasteners generally include a pair of legs adapted to penetrate tissue and connected by a backspan from which they extend. In use, subsequent to formation, some of the unitary fasteners have a "B" configuration. Typically, the two-part fastener includes legs that are barbed and connected by a backspan which are engaged and locked into a separate retainer piece that is usually located in the anvil. In use, the two-part fastener is pressed into the tissue so that the barbs penetrate the tissue and emerge from the other side where they are then locked into the retainer piece.

During each of the aforementioned surgical procedures, the tissue is initially gripped or clamped between the cartridge and anvil such that individual fasteners can be ejected from the cartridge, through the slots, and forced through the clamped tissue. Thereafter, the fasteners are formed by driving them into the depressions formed on the anvil.

A common concern in each of these procedures is hemostasis, or the rate at which bleeding of the target tissue is stopped. It is commonly known that by increasing the amount of pressure applied to a wound, the flow of blood can be limited, thereby decreasing the time necessary to achieve hemostasis. To this end, conventional surgical fastening apparatus generally apply two or more rows of fasteners about the cut-line to compress the surrounding tissue in an effort to stop any bleeding and to join the cut tissue together. Each of the fasteners will generally apply a compressive force to the tissue sufficient to effectuate hemostasis, however, if too much pressure is applied, this can result in a needless reduction in blood flow to the tissue surrounding the cut-line. Accordingly, the joining of tissue together in this manner may result in an elevated level of necrosis, a slower rate of healing, and/or a greater convalescence.

Consequently, it would be advantageous to provide a surgical fastening apparatus capable of limiting the flow of blood in the tissue immediately adjacent the cut tissue to effectuate hemostasis and wound closure, while maximizing blood flow in the surrounding tissue to facilitate healing.

Additionally, when tissue is clamped and compressed between the anvil and cartridge, some of the fluid of the tissue is squeezed out so the tissue is compressed further at the center portions of the cartridge and anvil than at the lateral edges, thereby leaving thicker tissue at the edges. It would therefore be advantageous to provide fasteners which could better accommodate these resulting different tissue thicknesses.

SUMMARY

The present disclosure provides in one aspect a surgical fastener applying apparatus comprising a cartridge body including a tissue contacting surface. The tissue contacting surface includes a plurality of fastener retention slots arranged in a plurality of rows including at least an inner row and an outer row. A plurality of surgical fasteners are disposed in inner and outer rows and configured such that the fasteners disposed in the inner row have a backspan that has a greater height than a backspan of the surgical fasteners disposed in the outer row. An anvil is provided having an inner row and an outer row of depressions for forming the fasteners. A plurality of pushers is operably associated with the plurality of surgical fasteners to eject the surgical fasteners toward a respective depression in the anvil for formation thereof such that upon formation the plurality of surgical fasteners ejected from the inner row provide a greater compressive force to tissue than the plurality of surgical fasteners ejected from the outer row.

In some embodiments, the plurality of rows of fasteners are spaced laterally on opposite sides of a channel that is located on the tissue contacting surface and configured to accommodate longitudinal movement of a knife.

Preferably, the surgical fasteners include two legs extending from a backspan and when formed include a generally "B" shape configuration forming a tissue compression space, wherein the tissue compression space of the plurality of surgical fasteners ejected from the inner row is less than the tissue compression space of the plurality of surgical fasteners ejected from the outer row.

In some embodiments, the two legs and the backspan include the same geometrical configuration such that the cross-sectional configuration of the surgical fastener is substantially uniform. In other embodiments, the two legs include a geometrical configuration that is different from a geometrical configuration of the backspan such that the cross-sectional configuration of the surgical fastener varies.

The apparatus may further comprise a third row of fasteners positioned between the first and second rows of fasteners wherein a plurality of surgical fasteners in the third row have a backspan having a height that is less than the height of the backspan of the plurality of surgical fasteners in the inner row and greater than the height of the backspan of the surgical fasteners in the outer row.

The cartridge body and anvil can be pivotally attached. Alternatively, at least one of the cartridge body and anvil can be movable along a substantially linear path to move the cartridge body and anvil into approximation. The inner and outer rows of fasteners can be arranged substantially linear. Alternatively, the inner and outer rows of fasteners can be arranged substantially annular.

The present disclosure also provides in another aspect a surgical fastener cartridge for use with a surgical fastener applying apparatus comprising a cartridge body including a plurality of fastener retention slots arranged in a plurality of rows including at least an inner row and an outer row. A plurality of first surgical fasteners are disposed in an inner row and a plurality of second surgical fasteners are disposed in an outer row. The plurality of first fasteners have a pair of legs extending from a backspan, the backspan having a first height that is greater than a second height of the backspan of the plurality of second surgical fasteners. A plurality of pushers operably associated with the plurality of surgical fasteners are configured to eject the surgical fasteners.

In some embodiments, the cartridge body includes a tissue contacting surface having a longitudinal channel configured to accommodate longitudinal movement of a knife, wherein a pair of inner rows of fasteners are positioned on opposite sides of the channel and a pair of outer rows of fasteners are positioned on opposite sides of the channel further from the channel than the pair of inner rows.

A pair of middle rows of fasteners can be provided positioned between the inner and outer rows of fasteners and having a backspan having third height greater than the second height and less than the first height.

Preferably, when formed, the surgical fasteners include a generally "B" shaped configuration wherein a tissue compression space of the plurality of surgical fasteners in the inner row is less than a tissue compression space of the plurality of surgical fasteners in the outer row.

In some embodiments, the two legs and the backspan include the same geometrical configuration such that the cross-sectional configuration of the surgical fastener is substantially uniform. Alternatively, the two legs include a geometrical configuration that is different from a geometrical configuration of the backspan such that the cross-sectional configuration of the surgical fastener varies.

The present disclosure also provides in another aspect a surgical fastener cartridge for use with a surgical fastener applying apparatus comprising a cartridge body including a plurality of fastener retention slots arranged in a plurality of rows including at least an inner row and an outer row, a plurality of surgical fasteners disposed in the inner and outer rows and configured such that the plurality of fasteners disposed in the inner row have a diameter that is greater than a diameter of the plurality of surgical fasteners disposed in the outer row, and a plurality of pushers operably associated with the plurality of surgical fasteners. The pushers eject the surgical fasteners toward a depression in an anvil such that upon formation of the surgical fasteners, the surgical fasteners ejected from the inner row define a first compression space and the surgical fasteners ejected from the outer row provide a second compression space larger than the first compression space.

In some embodiments, the plurality of rows are spaced laterally on opposite sides of a channel that is located on the tissue contacting surface and configured to accommodate longitudinal movement of a knife.

Preferably, each of surgical fasteners includes two legs connected by a backspan extending therebetween, the surgical fasteners including a generally "B" shape when formed.

In some embodiments, the plurality of retention slots and plurality of fasteners are arranged in a plurality of rows including at least an inner row, a middle row, and an outer row, wherein the fasteners disposed in the inner row have a diameter that is greater than a diameter of the surgical fasteners disposed in the middle row, and the surgical fasteners disposed in the middle row have a diameter that is greater than the surgical fasteners disposed in the outer row.

BRIEF DESCRIPTION OF THE DRAWINGS

Various embodiments of the present disclosure are described hereinbelow with references to the drawings, wherein:

FIG. 11A-1 is a side perspective cutaway view taken along line segment $A_1$-$A_1$ of the surgical fastener depicted in FIG. 11A;

FIGS. 14A₋₁-14C₋₁ illustrate side perspective cutaway views taken along line segments A₁-A₁, B₁-B₁, C₁-C₁ of the surgical fasteners depicted in FIGS. 14A-14C, respectively;

DETAILED DESCRIPTION OF EXEMPLARY EMBODIMENTS

Figure 1:
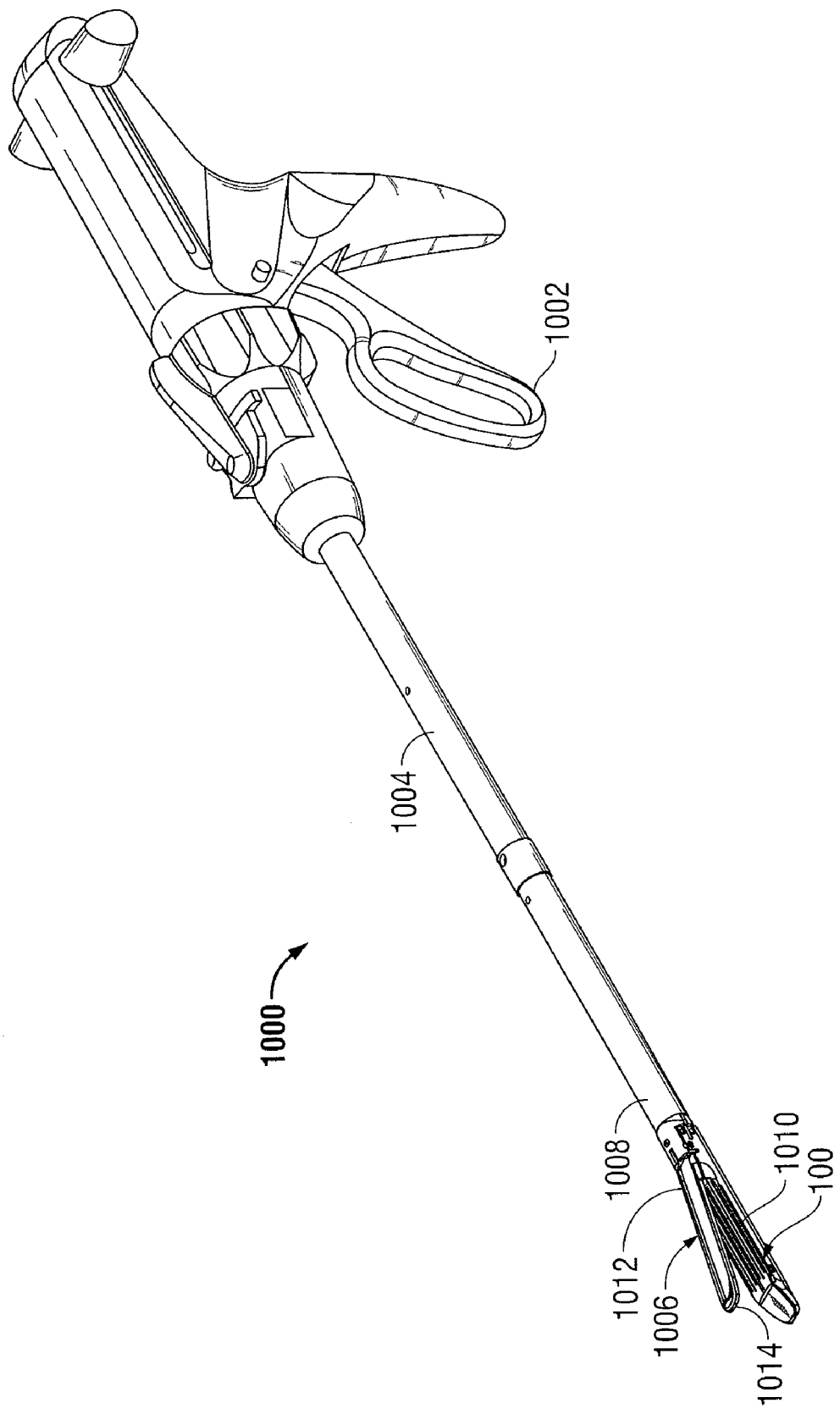
FIG. 1 illustrates an exemplary surgical fastener applying apparatus for use with a surgical fastener cartridge that employs surgical fasteners in accordance with embodiments of the present disclosure.

Various exemplary embodiments of the presently disclosed surgical fastener cartridge will now be described in detail with reference to the drawings wherein like references numerals identify similar or identical elements. In the drawings and in the description which follows, the term "proximal" will refer to the end of the surgical fastener cartridge that is closer to the operator during use, while the term "distal" will refer to the end of the fastener cartridge that is further from the operator, as is traditional and conventional in the art. In addition, the term "surgical fastener" should be understood to include any substantially rigid structure formed of a biocompatible material that is suitable for the intended purpose of joining tissue together, including but not being limited to surgical staples, clips, and the like.

The present disclosure provides a surgical fastener cartridge adapted to house a plurality of surgical fasteners providing varying degrees of compression force to stapled tissue occupied therein such that an effective hemostatic effect at or near the cut-line may be achieved. To this end, the surgical fasteners are configured such that the surgical fasteners deployed closer to the cut line produce a greater compression force to stapled tissue than the surgical fasteners deployed further from the cut line.

With reference to FIG. 1, a surgical fastener applying apparatus 1000 that employs a surgical fastener cartridge 100 is illustrated. Surgical fastener applying apparatus 1000 is used to sequentially apply a plurality of surgical fasteners to a patient's tissue. Surgical fastener apparatus 1000 may be configured for use, subsequent sterilization and reuse, or may be configured for single use. Surgical fastener applying apparatus 1000 includes a handle 1002, an elongated shaft or endoscopic portion 1004 extending distally therefrom, and an operative tool 1006 coupled to a distal end 1008 of the elongated shaft 1004. In general, operative tool 1006 is adapted to clamp, sequentially fasten together, and sever adjacent tissue segments along a cut-line. Operative tool 1006 includes a pair of opposed jaws 1012, 1010 pivotally coupled to one another and respectively including an anvil member 1014 that is approximated relative to cartridge 100 during use. The anvil includes depressions that are aligned with, and/or are in registration with slots 126 (FIG. 4) defined in the cartridge 100, through which the fasteners 130 will emerge, to effectuate formation. For a more detailed discussion of the approximation and firing of surgical fastener applying apparatus 1000, reference is made to commonly owned U.S. Pat. No. 5,865,361, currently assigned to Tyco Healthcare Group LP, the entire contents of which is incorporated herein by reference. In some embodiments, the cartridge and/or anvil is removable and replaceable.

Figure 2:
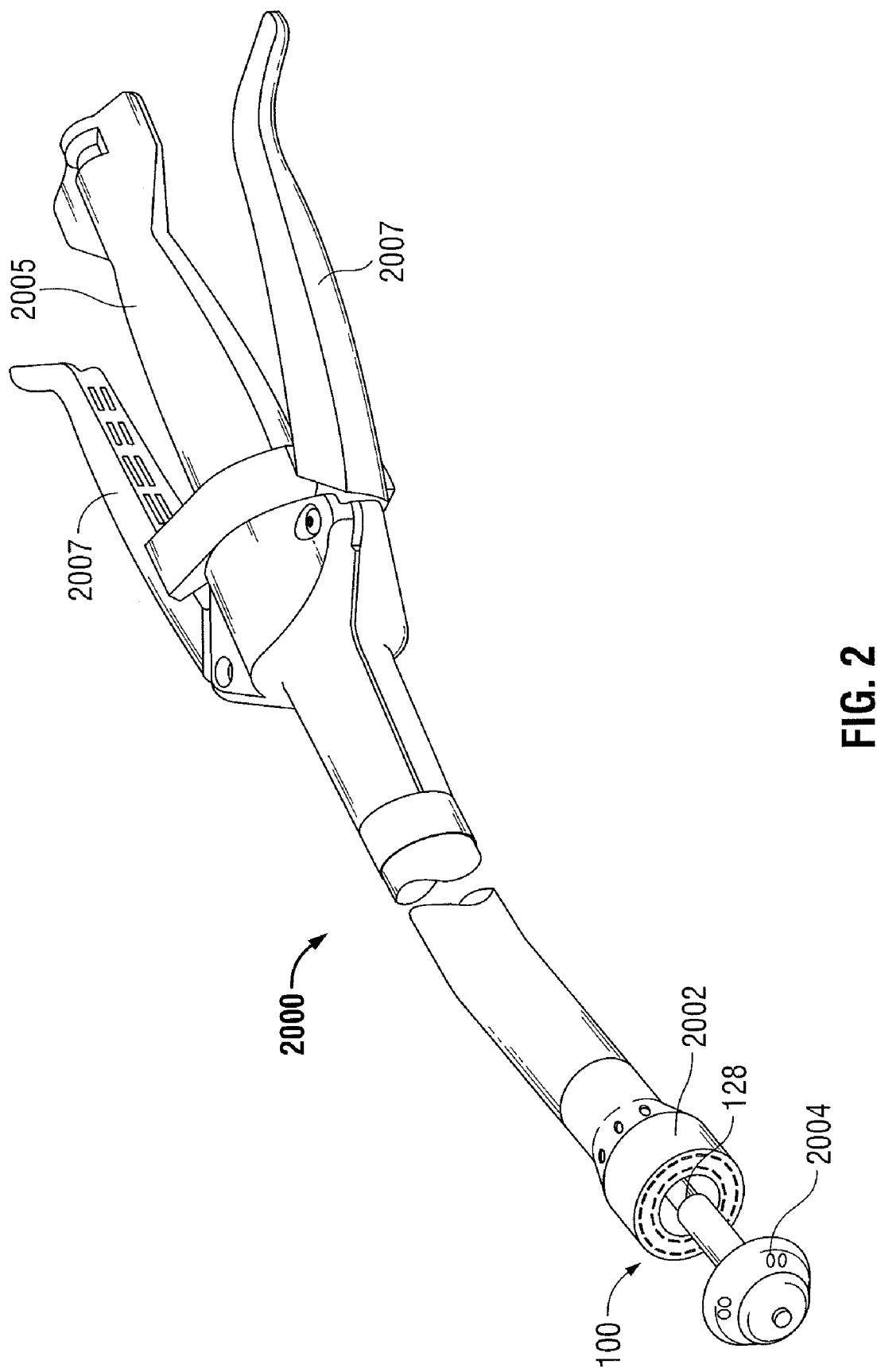
FIG. 2 illustrates another type of surgical fastener device that may employ an alternate embodiment of a surgical fastener cartridge in accordance with the present disclosure.
Figure 3:
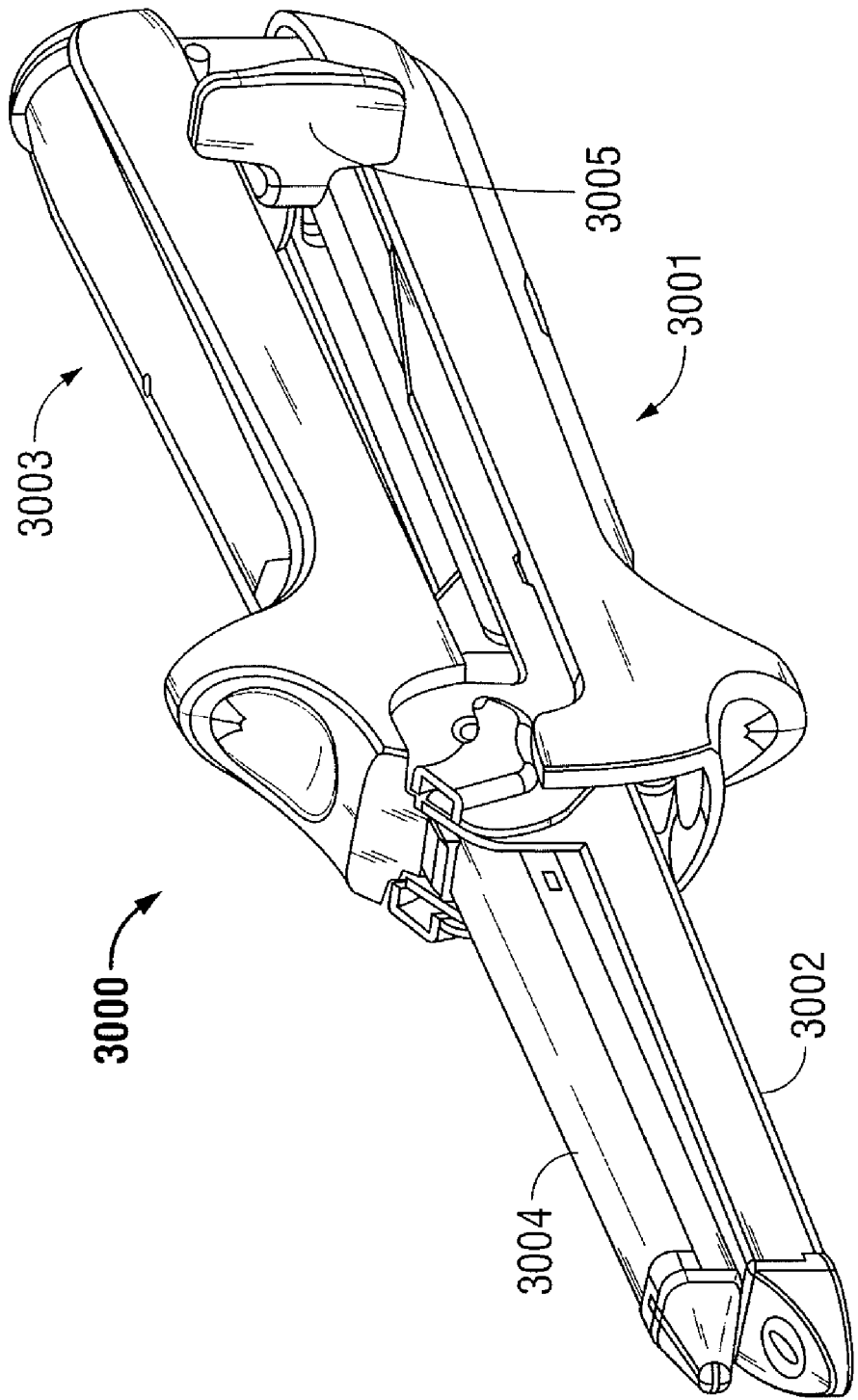
FIG. 3 illustrates another type of surgical fastener instrument that may employ an alternate embodiment of surgical fastener cartridge in accordance with the present disclosure.

While surgical fastener applying apparatus 1000 is depicted as an apparatus suitable for use in laparoscopic procedures for performing surgical anastomotic fastening of tissue, those skilled in the art will appreciate that cartridge 100 may be adapted for use with any surgical instrument suitable for the intended purposes described herein. For example, cartridge 100 may be adapted for use with an end-to-end anastomosis device 2000, as seen in FIG. 2, wherein the fasteners are arranged in substantially annular rows and/or a surgical stapling instrument 3000, as seen in FIG. 3, for use during an open gastro-intestinal anastomotic stapling procedure wherein the fasteners are arranged in substantially linear rows, or, for example, any of the surgical fastener applying apparatus disclosed in U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, which are each incorporated by reference herein in their entirety. The cartridge in preferred embodiments is removable and replaceable with another loaded cartridge for use with these apparatus.

For the purposes of brevity, the structural and operational features of cartridge 100 will be described in terms of use with the surgical fastener applying apparatus 1000.

Figure 4:
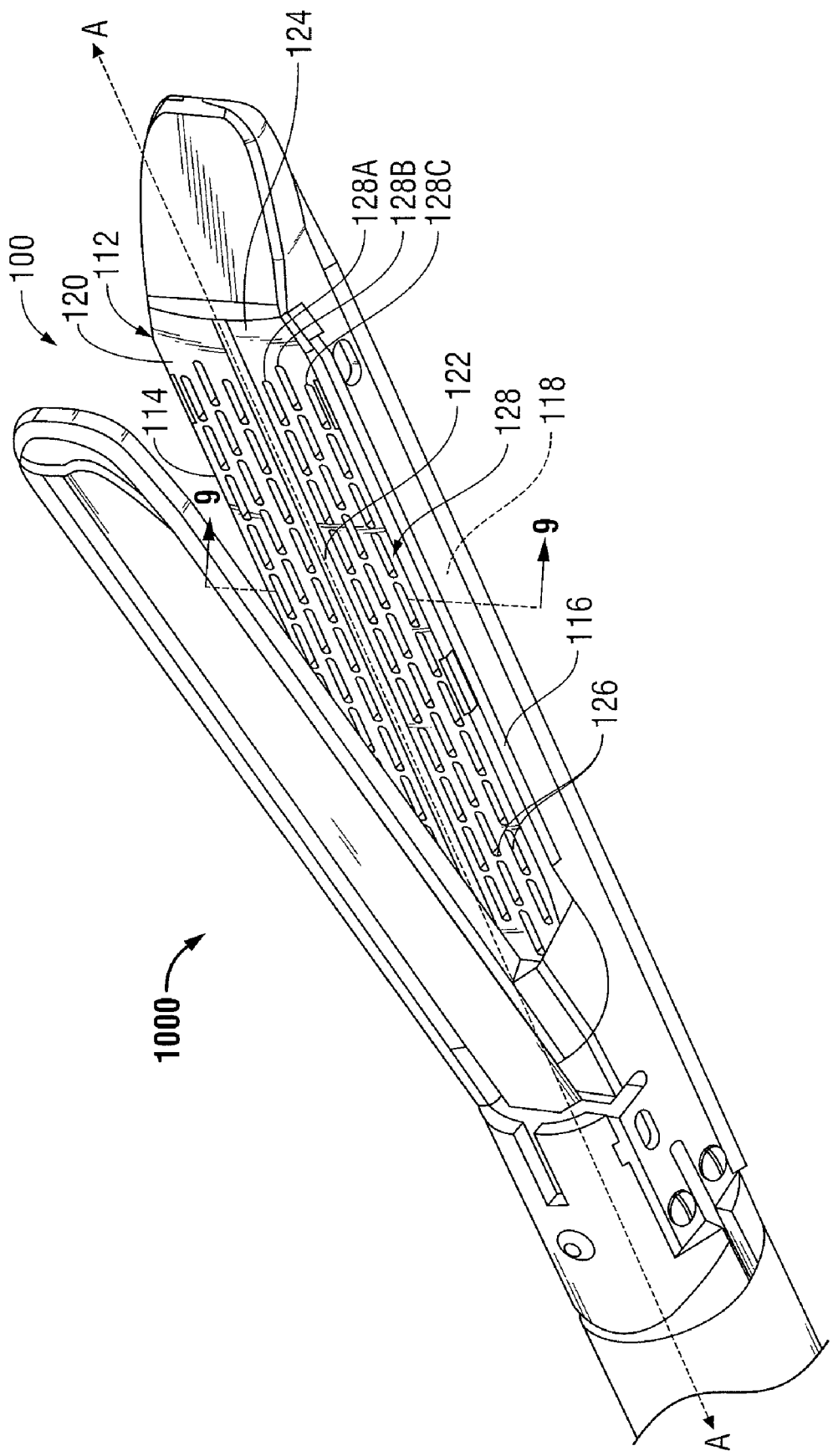
FIG. 4 is a top perspective view of a surgical fastener cartridge shown in the distal end portion of the surgical fastener device depicted in FIG. 1.

With reference to FIG. 4, cartridge 100 of tool assembly 1006 is shown. Cartridge 100 extends along a longitudinal axis "A-A" and includes a cartridge body 112 with a pair of side walls 114, 116, a bottom wall 118, and a top wall 120. The top wall 120 includes a knife slot or channel 122 that is configured to accommodate longitudinal movement of a knife (not shown), or other suitable cutting element, such that stapled tissue may be severed along a cut-line. The top wall 120 further includes a tissue engaging surface 124 (e.g., for maintaining the position of the tissue to be cut) and a plurality of fastener retention slots 126 arranged into a plurality of rows 128 that extend substantially the length of the cartridge 100. As shown in FIG. 4, the fastener retention slots 126 are arranged into a pair of first (inner) rows 128$_A$ that are spaced laterally from the knife slot 122 and on opposite sides thereof, a pair of second (middle) rows 128$_B$ that are spaced laterally from the pair of first rows 128$_A$ and on opposite sides of the knife slot 122, and a pair of third (outer) rows 128$_C$ that are spaced laterally from the pair of second rows 128$_B$ and on opposite sides of knife slot 122. While the cartridge 100 is depicted as including pairs of first, second, and third rows 128$_A$, 128$_B$, 128$_C$, respectively, it is within the purview of the present disclosure to have more or fewer rows of the fastener retention slots 126 (and fasteners) disposed on cartridge 100. Additionally, rows 128 may extend radially from the cutting element in an annular array; such is the case when the fastening cartridge is employed with the surgical fastening device depicted in FIG. 2.

Figure 9:
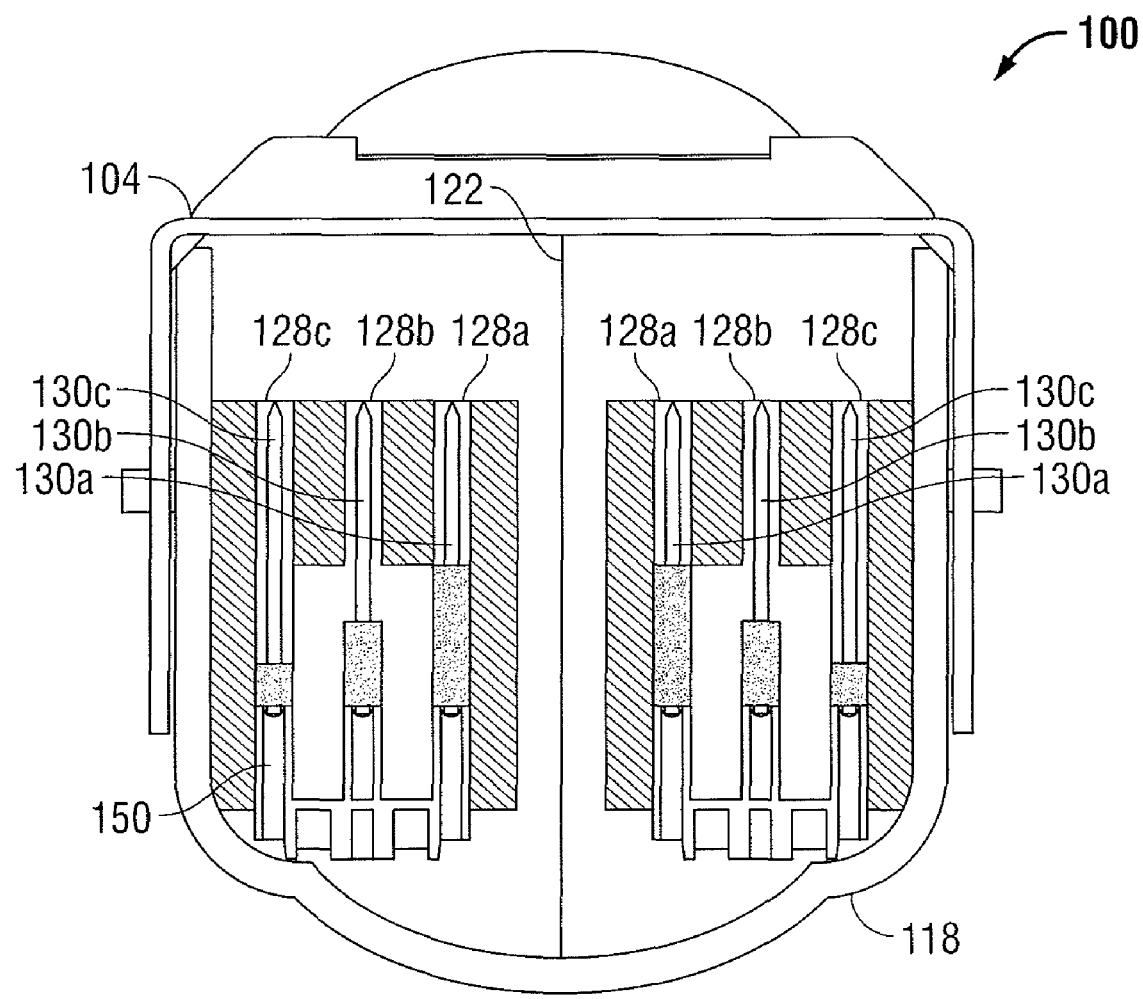
FIG. 9 is partial cross-sectional view taken along the line segment "9-9" in FIG. 4 illustrating the surgical fastener cartridge loaded with the surgical fasteners depicted in FIGS. 8A-8C.

Each of the fastener retention slots 126 is configured to receive one of a plurality of surgical fasteners 130 and pushers 150 therein such that the surgical fasteners 130 are deployed in rows (e.g., inner, middle, and outer rows) on opposite sides of the cut-line created in the tissue during fastening, as shown in FIG. 9.

For a more detailed description of the functional and structural features of cartridge 100, reference is made to commonly owned U.S. Pat. No. 7,070,083 the entire contents of which are incorporated by reference herein.

With reference now to FIGS. 5, and 6A-6D, cartridge 100 is loaded with one or more varieties of surgical fastener, represented generally as surgical fastener 130. Surgical fastener 130 of cartridge 100 is configured such that the surgical fastener 130 deployed closer to the cut line provides a greater compression force to the stapled tissue than the surgical fastener 130 deployed further from the cut line. To this end, surgical fastener 130 includes two legs 132 extending from a backspan 134 extending therebetween. The thickness of the backspan 134 and the legs 132 can be varied such that the surgical fastener 130 closer to the cut line provides a greater compression force to stapled tissue occupied therein than the surgical fastener 130 further from the cut line. The thickness of the backspan 134 and the legs 132 may also be varied to fasten adjacent tissue segments "$T_1$", "$T_2$" of varying thickness.

The legs 132 and the backspan 134 may define a cross-section having any suitable geometric configuration, including but not limited to rectangular, oval, square, triangular, and trapezoidal. The legs 132 and the backspan 134 may exhibit the same geometrical configuration such that the cross-sectional configuration of the surgical fastener 130 is substantially uniform, or, alternatively, the legs 132 and the backspan 134 may exhibit different geometrical configurations, e.g., the legs 132 may exhibit a rectangular cross-section and the backspan 34 may exhibit an oval cross-section, as shown in for example in FIGS. 6A-6D discussed in more detail below. Backspan 134 and/or legs 132 may be formed by any suitable means known in the art including but not limited to welding, braising, coining, casting, overmolding and so on. Additionally, backspan may include different configurations of blocking and/or retainer material, tube, sleeve, collar, and/or grommet.

Figure 5:
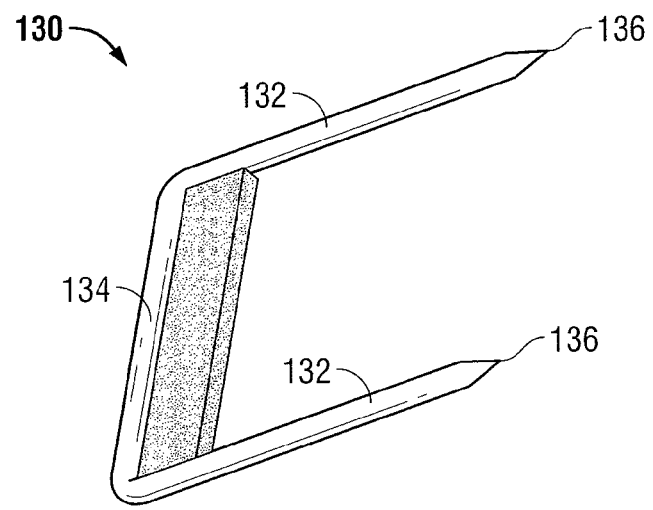
FIG. 5 is a side perspective view one embodiment of the surgical fastener configured for use with the cartridge depicted in FIG. 4 including a backspan having a first height and shown prior to formation.

As seen in FIG. 5, prior to the formation of surgical fastener 130, legs 132 extend from the backspan 134 such that they are substantially parallel. Alternatively, the legs 132 may converge or diverge from the backspan. The present disclosure contemplates that the surgical fastener 130 may also be configured as a directionally biased staple, such as those described in commonly owned U.S. Pat. No. 7,398,907, the entire contents of which are incorporated by reference herein.

Each of the legs 132 terminates in a penetrating end 136 that is configured to penetrate tissue (tissue segments "$T_1$", "$T_2$" for example) and/or other suitable material (blocking and/or retainer material for example). The penetrating ends 136 of legs 132 can be tapered to facilitate the penetration of tissue segments "$T_1$", "$T_2$", or alternatively, the penetrating ends 136 may not include a taper. In various embodiments, penetrating ends 136 may define a conical or flat surface, as described in co-pending U.S. patent application Ser. No. 11/444,761, filed Apr. 13, 2003, the entire contents of which are incorporated by reference herein. In some embodiments, one or both of legs 132 may be barbed. Having legs 132 configured in such a manner may facilitate maintaining the surgical fastener 130 in a fixed position within the tissue and/or blocking material.

Figure 7:
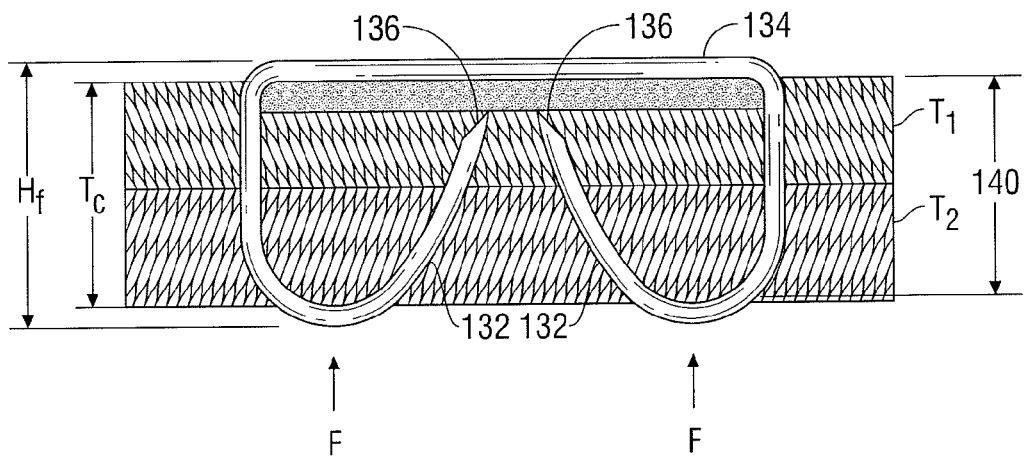
FIG. 7 is a side perspective view of the surgical fastener depicted in FIG. 5 shown subsequent to formation and within adjacent tissue segments.

Turning now to FIG. 7, surgical fastener 130 is shown subsequent to formation. Surgical fastener 130 is configured to provide a compression force to stapled tissue occupied therein. To this end, legs 132 cooperate with backspan 134 to maintain adjacent tissue segments "$T_1$", "$T_2$" in approximation and apply a compressive force "F" thereto. The compressive force "F" applies pressure to the tissue segments "$T_1$", "$T_2$", thereby restricting the flow of blood through the tissue surrounding the surgical fastener 130 and facilitating hemostasis. The configuration of the backspan 134 may limit the amount of pressure that can be applied to the tissue segments "$T_1$", "$T_2$" such that the flow of blood through the tissue is not completely restricted. When formed, the surgical fastener 130 has a generally "B" shape with an overall height "$H_F$" (measured from the backspan 134 to the outermost curve of the legs 132), and a tissue compression space 140.

Figure 8A:
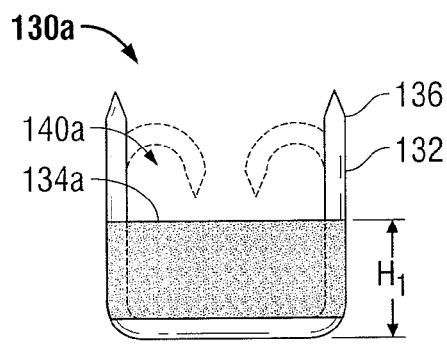
FIGS. 8A-8C illustrate the surgical fastener depicted in FIG. 7 shown having three different backspan heights and being shown prior to and subsequent to formation (in phantom)
Figure 8B:
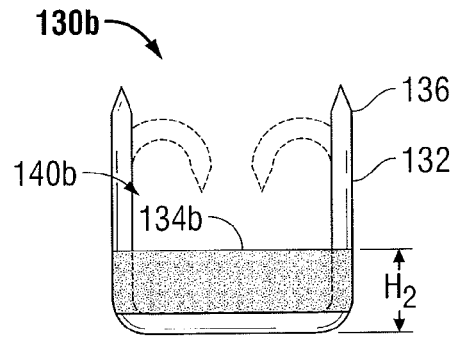
Figure 8C:
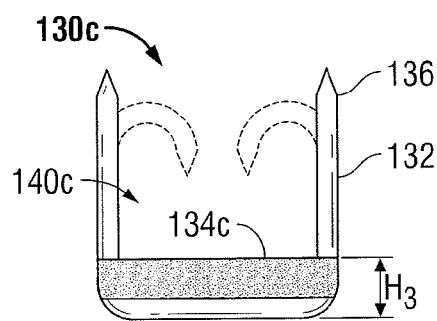

With reference to FIGS. 8A-8C, surgical fastener 130 will be described in terms of surgical fasteners $130_A$, $130_B$, and $130_C$. Surgical fasteners $130_A$, $130_B$, and $130_C$ are respectively shown in their initial and formed conditions (in phantom). Surgical fasteners $130_A$, $130_B$, $130_C$, are substantially similar to each other but for the dimensions of the respective backspan 134. The overall heights of the surgical fasteners $130_A$, $130_B$ and $130_C$, in the unformed condition (measured from the penetrating tip to the outermost surface of the backspan) and in the formed condition (measured from the outermost curve of the legs to the outermost surface of the backspan) are shown as being substantially equal. Thus, the lengths of the legs of the fasteners $130_A$, $130_B$ and $130_C$ in the unformed condition are in a preferred embodiment substantially equal. The heights "$H_1$", "$H_2$", and/or "$H_3$" of the backspan may be altered, which, in turn, will alter the dimensions of the compressive spaces $140_A$, $140_B$, $140_C$ occupied by stapled tissue segments "$T_1$", "$T_2$" when the respective surgical fasteners $130_A$, $130_B$, $130_C$ are in their formed conditions. By altering the respective dimensions of "$H_1$", "$H_2$", and/or "$H_3$" any desired level of hemostasis and blood flow in the stapled tissue segments "$T_1$", "$T_2$" may be effectuated. Other various attributes of the tissue (e.g., thickness or the presence of scar tissue) may increase or diminish the level of hemostasis and blood flow in the stapled tissue segments.

Surgical fastener $130_C$ includes backspan $134_C$ that extends towards the penetrating ends 136 of the legs 132 and has a height "$H_3$". When the surgical fastener $130_C$ is formed (phantomly shown in FIG. 8C) within tissue segments "$T_1$", "$T_2$", the backspan $134_C$ cooperates with the legs 132 of the surgical fastener $130_C$ to form tissue compressive space $140_C$ (FIG. 8C). Compression space or zone $140_C$ provides minimal blood flow restriction when the tissue segments are stapled together.

Surgical fastener $130_B$ includes backspan $134_B$ that extends towards the penetrating ends 136 of the legs 132 and has a height "$H_2$". When the surgical fastener $130_B$ is formed (phantomly shown in FIG. 8B) within tissue segments "$T_1$", "$T_2$", the backspan $134_B$ cooperates with the legs 132 of the surgical fastener $130_B$ to form tissue compression space $140_B$ (FIG. 8B). The compression space $140_B$ is less than the compression space $140_C$ of fastener $130_C$. Accordingly, because the pressure exerted on the tissue segments "$T_1$", "$T_2$" by surgical fastener $130_B$ is greater than the pressure exerted on the tissue segments "$T_1$", "$T_2$" by surgical fastener $130_C$, the blood flow through the tissue surrounding surgical fastener $130_B$ will be less (more restricted) than the blood flow through the tissue surrounding surgical fastener $130_C$, thereby further facilitating hemostasis. However, because blood flow is not completely restricted through tissue compression space $140_B$, unnecessary necrosis of the stapled tissue may be prevented and/or impeded.

Surgical fastener $130_A$ includes backspan $134_A$ that extends towards the penetrating ends 136 of the legs 132 and has a height "$H_1$". When the surgical fastener $130_A$ is formed (phantomly shown in FIG. 8A) within tissue segments "$T_1$", "$T_2$", the backspan $134_A$ cooperates with the legs 132 of the surgical fastener $130_A$ to form tissue compression space $140_A$ (FIG. 8A). The compression space $140_A$ is less than the compression space $140_B$ of fastener $130_B$. Accordingly, because the pressure exerted on the tissue segments "$T_1$", "$T_2$" by surgical fastener $130_A$ is greater than the pressure exerted on the tissue segments "$T_1$", "$T_2$" by surgical fasteners $130_B$, $130_C$, the blood flow through the tissue surrounding surgical fastener $130_A$ will be less (more restricted) than the blood flow through the tissue surrounding surgical fasteners $130_B$, $130_C$, thereby further facilitating hemostasis. Because blood flow is substantially, if not completely restricted, through tissue compression space $140_A$ this results in further facilitating and effectuating hemostasis.

FIG. 9 illustrates the surgical fasteners $130_A$, $130_B$, and $130_C$ loaded within the cartridge body 112 shown in FIGS. 1 and 4. The surgical fasteners $130_A$, $130_B$, and $130_C$ are arranged to define a pair of inner, middle, and outer rows $128_A$, $128_B$, and $128_C$, respectively, of fastener retention slots 126 formed in the top wall 120. The pair of inner, middle, and outer rows $128_A$, $128_B$, and $128_C$, respectively, are each spaced laterally from the knife slot 122, on opposite sides thereof, such that the surgical fasteners $130_A$, $130_B$, and $130_C$ will be deployed on opposite sides of the cut-line (not shown) created in the tissue upon fastening. That is, the fasteners $130_A$ with the largest height backspan provide a greater compressive force as there is a shorter distance between the inner surface of the backspan and the curve of the formed legs, and in the illustrated embodiment are provided in the inner rows closer to the cut line. The fasteners $130_B$ have a greater distance between the curve of the legs and the inner surface of the backspan and are provided on the outer rows where the tissue might be thicker as a result of clamping by the instrument jaws (anvil and cartridge). If a third row of fasteners $130_C$ is used in this embodiment, then the fasteners of FIG. 8C with the smallest height backspan (largest compression space) would preferably be placed on the outermost row furthest from the cut line. By providing the rows of fasteners which provide greater tissue compression as you approach the cut line, a greater range of tissue thicknesses can be effectively sealed by the same cartridge. It should be appreciated, however, that the fasteners can be placed on other rows than the foregoing. Also, while the inner, middle, and outer rows $128_A$, $128_B$, and $128_C$, respectively, are shown as including the surgical fasteners $130_A$, $130_B$, $130_C$, respectively, the present disclosure contemplates the inclusion of the fasteners in other rows or arrangement of any of the surgical fasteners $130_A$, $130_B$, and $130_C$, disclosed herein above, either exclusively, such that only a single surgical fastener, e.g., surgical fastener 130, is present in a particular row, or in combination, such that a variety of surgical fasteners, e.g., surgical fasteners $130_A$, $130_B$, and $130_C$, are present in one or more rows.

In one particular embodiment, the outer rows $128_C$, intermediate rows $128_B$, and inner rows $128_A$ are comprised solely of surgical fasteners $130_C$, $130_B$, and $130_A$, respectively such that the flow of blood through the tissue immediately surrounding the cut-line (not shown) is substantially, if not completely, restricted by the inner row $128_A$ of surgical fasteners $130_A$, whereas the flow of blood through the tissue surrounding the intermediate and outer rows $128_B$, $128_C$ is less restricted by surgical fasteners $130_B$, $130_C$, respectively. Accordingly, the flow of blood is minimized in the tissue immediately adjacent the cut-line and is increased gradually as the lateral distance from the cut-line is also increased. Also by this arrangement, the fasteners with the largest height backspan (fasteners $130_A$), are closest to the cut line where the tissue is generally compressed to the greater extent and the fasteners with the smaller height backspan are positioned in the outer rows where the tissue is thicker. It should be appreciated that the height of the backspans could be varied to accommodate tissue of different thicknesses and to control tissue compression by the fasteners.

Figure 6A:
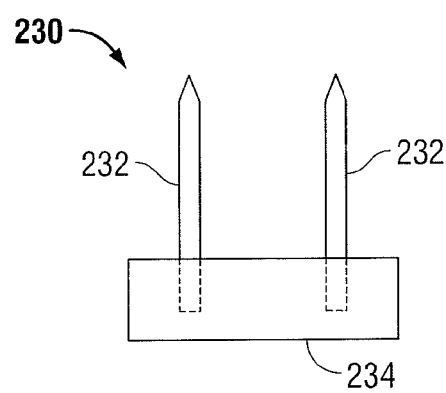
FIGS. 6A-6D illustrate different surgical fasteners that include different backspan configurations in accordance with alternate embodiments of the present disclosure.
Figure 6B:
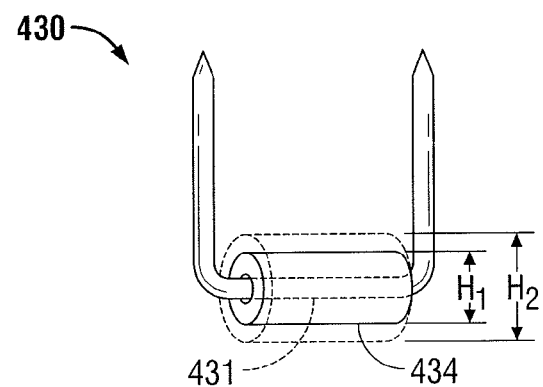
Figure 6C:
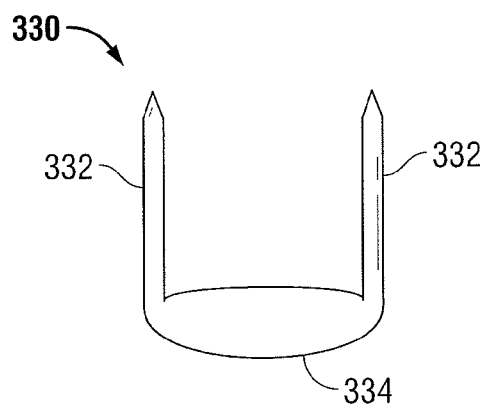
Figure 6D:
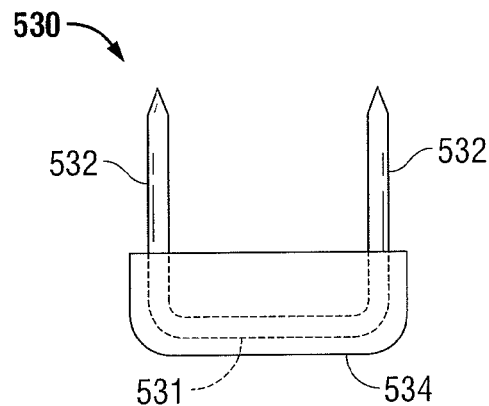

In the embodiment of FIGS. 5 and 7, the backspan height is varied by attachment of a separate material to the fastener, such as thermoplastic, by way of example. It can be attached by methods such as insert molding. In the embodiment of FIG. 6A, the backspan is an integral element 234 in which the fastener legs 232 are embedded. In FIG. 6C, the backspan 334 is integral with the fastener legs 332. In the embodiments of FIGS. 6B and 6D, a separate backspan material is attached to the fastener 430, 530, respectively, with backspan 434 of FIG. 6B being in the form of a cylindrical collar encircling the backspan portion 431 of the fastener 430 and the backspan 534 of fastener 530 of FIG. 6D encompassing the backspan portion 531 of the fastener and a portion of the fastener legs 532. The backspan material of FIGS. 6B and 6D can be composed of thermoplastic overmolded on the staple wire by way of example. Varying the thickness or height of these backspans by varying the height of the integral backspans or the backspan materials can vary the compression force of the formed staple by varying the distance between the curved legs and inner portion of the backspan as described in detail above with respect to fastener 130. FIG. 6B illustrates this by showing in phantom a collar of larger diameter to decrease the compression area. Other backspan shapes and attachments to achieve the various compression forces are also contemplated.

Figure 10:
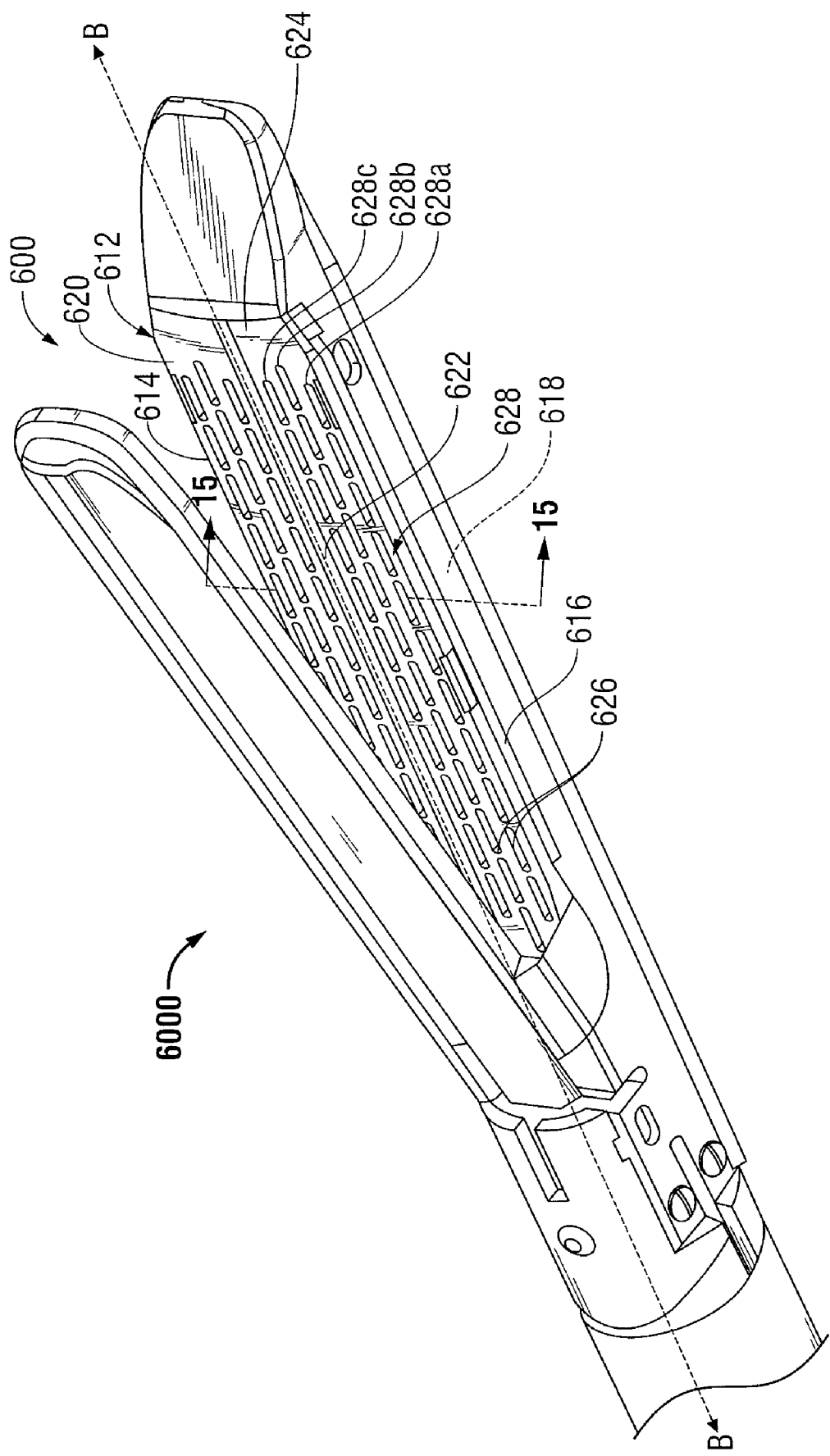
FIG. 10 is a top perspective view of a surgical fastener cartridge that is suitable for use with the surgical fastener device depicted in FIG. 1.

With reference now to FIGS. 10-15, and initially with reference to FIG. 10, an alternate embodiment of a surgical fastener cartridge is illustrated and is shown generally as 600 and described.

For the purposes of brevity, the structural and operational features of cartridge 600 will be described in terms of use with the surgical fastener applying apparatus 1000.

With reference to FIG. 10, cartridge 600 is shown. Cartridge 600 extends along a longitudinal axis "B-B" and includes a cartridge body 612 with a pair of side walls 614, 616, a bottom wall 618, and a top wall 620. The top wall 620 includes a channel or knife slot 622 that is configured to accommodate longitudinal movement of a knife (not shown), or other suitable cutting element, such that stapled tissue may be severed along a cut-line. The top wall 620 further includes a tissue engaging surface 624 (e.g., for maintaining the position of the tissue to be cut) and a plurality of fastener retention slots 626 arranged into a plurality of rows 628 that extend substantially the length of the cartridge 600. As shown in FIG. 10, the fastener retention slots 626 are arranged into a pair of first (inner) rows $628_C$ that are spaced laterally from the knife slot 622 and on opposite sides thereof, a pair of second (middle) rows $628_B$ that are spaced laterally from the pair of first rows $628_C$ and on opposite sides of the knife slot 622, and a pair of third (outer) rows $628_A$ that are spaced laterally from the pair of second rows $628_B$ and on opposite sides of knife slot 622. While the cartridge 100 is depicted as including pairs of first, second, and third rows $628_C$, $628_B$, $628_A$, respectively, it is within the purview of the present disclosure to have more or fewer rows of the fastener retention slots 626 (or fasteners) disposed on cartridge 100. Additionally, rows 628 may extend radially from the cutting element; such is the case when the fastening cartridge is employed with the surgical fastening device depicted in FIG. 2.

Figure 15:
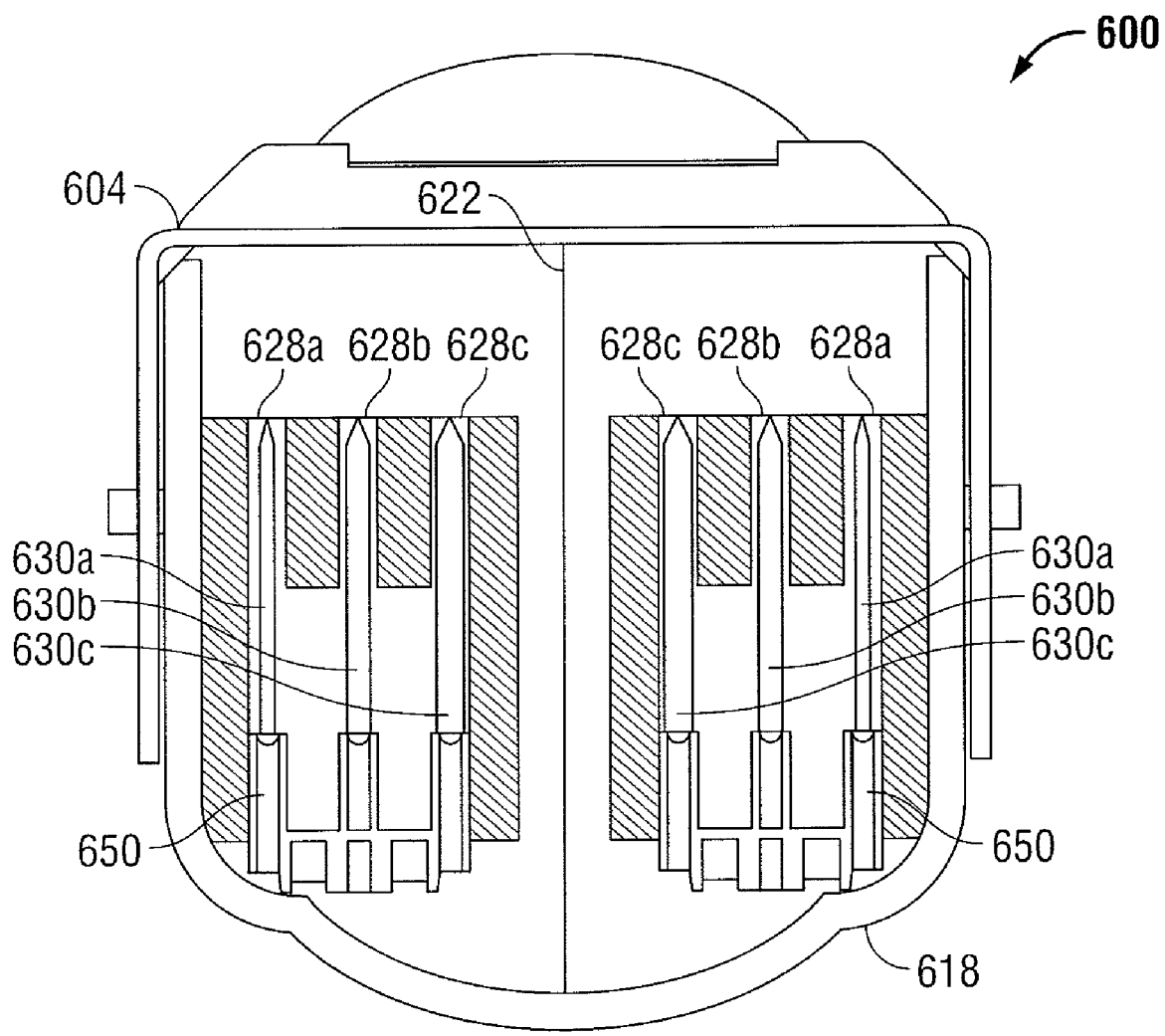
FIG. 15 is partial cross-sectional view taken along the line segment "15-15" in FIG. 10 illustrating the surgical fastener cartridge loaded with the surgical fasteners depicted in FIGS. 14A-14C.

Each of the fastener retention slots 626 is configured to receive one of a plurality of surgical fasteners 630 and pushers 650 therein such that the surgical fasteners 630 are deployed in rows (e.g., inner, middle, and outer rows) on opposite sides of the cut-line created in the tissue during fastening, as shown in FIG. 15.

For a more detailed description of the functional and structural features of cartridge 600, reference is made to commonly owned U.S. Pat. No. 7,070,083 the entire contents of which are incorporated by reference herein.

Figure 11A:
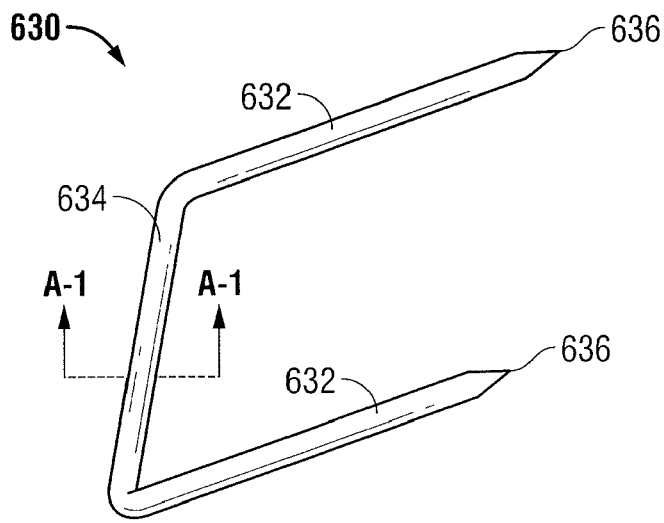
FIG. 11A is a side perspective view of the surgical fastener configured for use with the cartridge depicted in FIG. 10 having a first diameter and shown prior to formation.

With reference now to FIGS. 11A and $11_{A-1}$ and 12A-12D, cartridge 600 may loaded with one or more varieties of surgical fastener, represented generally as surgical fastener 630. Surgical fastener 630 of cartridge 600 is configured such that the surgical fastener 630 deployed closer to the cut line provides a greater compression force to the stapled tissue than the surgical fastener 630 deployed further from the cut line. To this end, surgical fastener 630 includes two legs 632 connected by a backspan 634 extending therebetween. The thickness of the backspan 634 and the legs 632 can be varied such that the surgical fastener 630 closer to the cut line provides a greater compression force to stapled tissue occupied therein than the surgical fastener 630 further from the cut line. The thickness of the backspan 634 and the legs 632 may also be varied to fasten adjacent tissue segments "$T_1$", "$T_2$" of varying thickness.

The legs 632 and the backspan 634 may define a cross-section having any suitable geometric configuration, including but not limited to rectangular, oval, square, triangular, and trapezoidal. The legs 632 and the backspan 634 may exhibit the same geometrical configuration such that the cross-sectional configuration of the surgical fastener 630 is substantially uniform, as shown in FIG. 11A, or, alternatively, the legs 632 and the backspan 634 may exhibit different geometrical configurations, e.g., the legs 632 may exhibit a rectangular cross-section and the backspan 634 may exhibit an oval cross-section, as shown in FIGS. 12A-12D. Backspan 634 and/or legs 632 may be formed by any suitable means known in the art including but not limited to welding, braising, coining, casting, overmolding and so on. Additionally, backspan 634 and/or legs 632 may be treated by way of annealing, cold working, heat treating, and so on. This may provide increased burst strength to the surgical fastener. Moreover, backspan may include different configurations of blocking and/or retainer material, tube, sleeve, collar, and/or grommet.

As seen in FIG. 11A, prior to the formation of surgical fastener 630, legs 632 extend from the backspan 634 such that they are substantially parallel. Alternatively, the legs 632 may converge or diverge from the backspan. The present disclosure contemplates that the surgical fastener 630 may also be configured as a directionally biased staple, such as those described in commonly owned U.S. Pat. No. 7,398,907, the entire contents of which are incorporated by reference herein.

Each of the legs 632 terminates in a penetrating end 636 that is configured to penetrate tissue (tissue segments "$T_1$", "$T_2$" for example) and/or other suitable material (blocking and/or retainer material for example). The penetrating ends 636 of legs 632 can be tapered to facilitate the penetration of tissue segments "$T_1$", "$T_2$", or alternatively, the penetrating ends 636 may not include a taper. In various embodiments, penetrating ends 636 may define a conical or flat surface, as described in co-pending U.S. patent application Ser. No. 11/444,761, filed Apr. 13, 2003, the entire contents of which are incorporated by reference herein. In some embodiments, one or both of legs 632 may be barbed. Having legs 632 configured in such a manner may facilitate maintaining the surgical fastener 630 in a fixed position within the tissue and/or blocking material.

Figure 13:
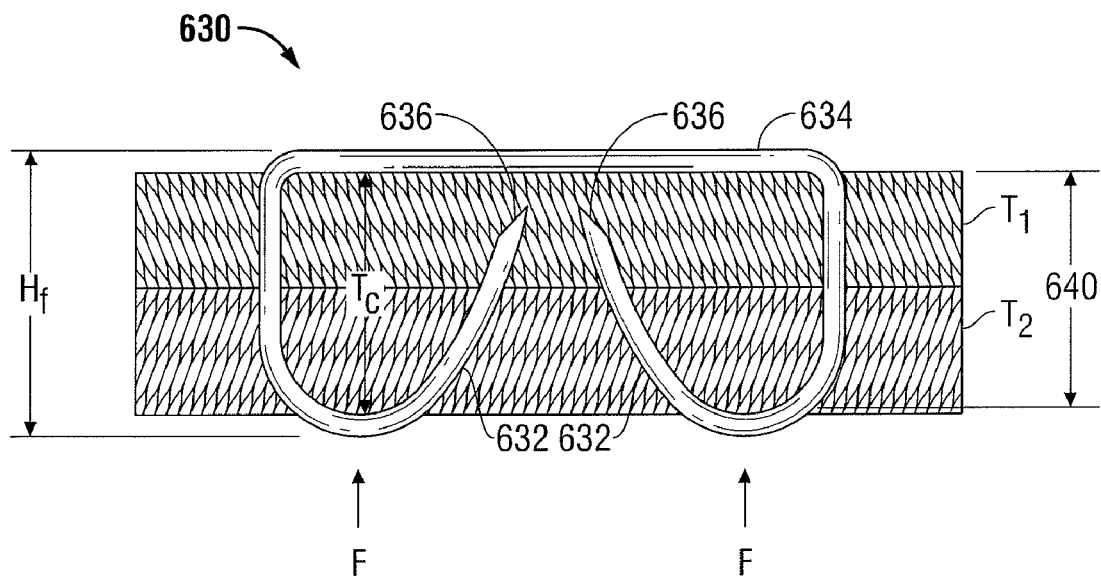
FIG. 13 is a side perspective view of the surgical fastener depicted in FIG. 11A shown subsequent to formation and within adjacent tissue segments.

Turning now to FIG. 13, surgical fastener 630 is shown subsequent to formation. Surgical fastener 630 is configured to provide a compression force to stapled tissue occupied therein. To this end, legs 632 cooperate with backspan 634 to maintain adjacent tissue segments "$T_1$", "$T_2$" in approximation and apply a compressive force "F" thereto. The compressive force "F" applies pressure to the tissue segments "$T_1$", "$T_2$", thereby restricting the flow of blood through the tissue surrounding the surgical fastener 130 and facilitating hemostasis. The linear configuration of the backspan 634 may limit the amount of pressure that can be applied to the tissue segments "$T_1$", "$T_2$" such that the flow of blood through the tissue is not completely restricted. When formed, the surgical fastener 630 has a generally "B" shape with an overall height "$H_E$" (measured from the outermost surface of the backspan 634 to the outermost curve of the legs 632) and a tissue compression space 640.

With reference to FIGS. 14A-14C, and FIGS. 14A-1-14C-1, respectively, surgical fastener 630 will be described in terms of surgical fasteners $630_A$, $630_B$, and $630_C$. Surgical fasteners $630_A$, $630_B$, and $630_C$ are respectively shown in their initial and formed conditions (in phantom). Surgical fasteners $630_A$, $630_B$, $630_C$, are substantially similar to each other but for their respective diameters. The overall heights of the surgical fasteners $630_A$, $630_B$, $630_C$, in the unformed condition (measured from the penetrating tip of the legs to the outermost surface of the backspan) are shown as being substantially equal. Thus, in a preferred embodiment, the length of the legs of the fasteners $630_A$, $630_B$, $630_C$ in the unformed condition are substantially equal. The respective dimensions "$D_3$", "$D_2$", and/or "$D_1$" of surgical fasteners $630_C$, $630_B$ and/or $630_A$, may be altered, which, in turn, will alter the dimensions of the compressive spaces $640_C$, $640_B$, $640_A$ occupied by stapled tissue segments "$T_1$", "$T_2$" when the respective surgical fasteners $630_C$, $630_B$, $630_A$ are in their formed conditions. Surgical fasteners having larger diameters (or transverse cross-sections) form a "B" shape with a smaller tissue compression space 640 and surgical fasteners having smaller diameters (transverse cross-sections) form a "B" shape with a larger tissue compression space 640. By altering the respective dimensions of "$D_3$", "$D_2$", and/or "$D_1$" any desired level of hemostasis and blood flow in the stapled tissue segments "$T_1$", "$T_2$" may be effectuated. Other various attributes of the tissue (e.g., thickness or the presence of scar tissue) may increase or diminish the level of hemostasis and blood flow in the stapled tissue segments.

Figures 1, 14A:
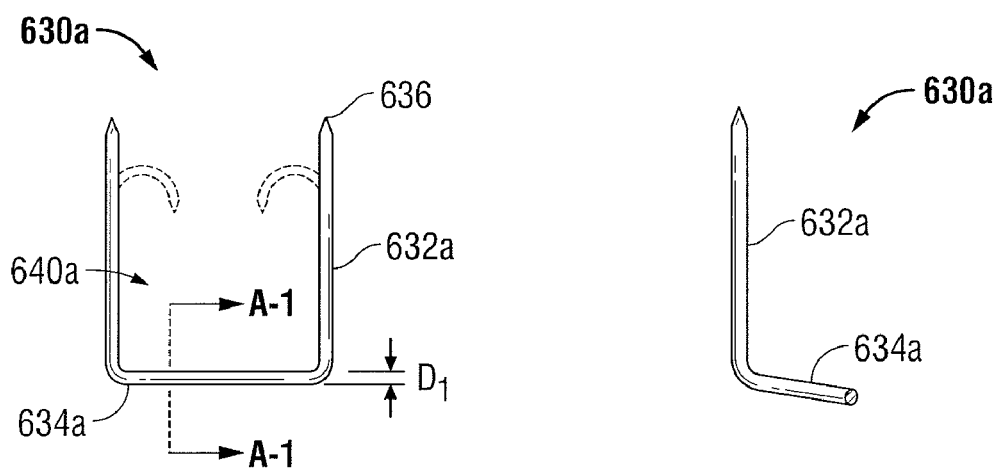
FIGS. 14A-14C illustrate the surgical fastener depicted in FIG. 13 shown having three different diameters and being shown prior to and subsequent to formation (in phantom)

Surgical fastener $630_A$ has a diameter "$D_1$". When the surgical fastener $630_A$ is formed (phantomly shown in FIG. 14A) within tissue segments "$T_1$", "$T_2$", the backspan $634_A$ cooperates with the legs $632_A$ of the surgical fastener $630_A$ to form tissue compressive spaces $640_A$ (FIG. 14A). Compression space or zone $640_A$ provides minimal blood flow restriction when the tissue segments are stapled together.

Figure 14B:
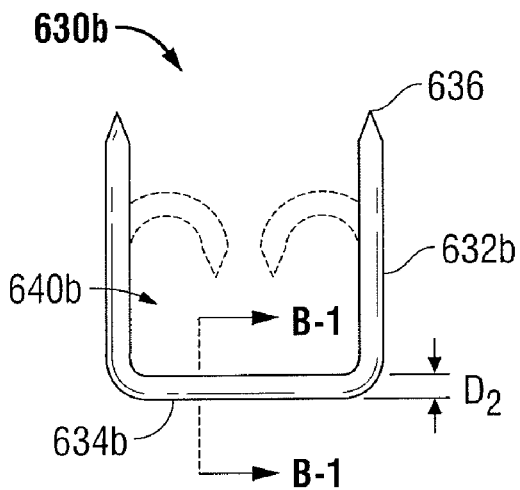
Figures 1, 14B:
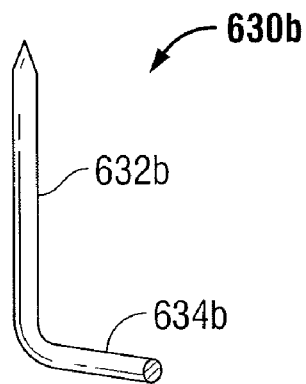

Surgical fastener $630_B$ has a diameter "$D_2$", greater than the diameter "$D_1$" of fastener $630_A$. When the surgical fastener $630_B$ is formed (phantomly shown in FIG. 14B) within tissue segments "$T_1$", "$T_2$", the backspan $634_B$ cooperates with the legs $632_B$ of the surgical fastener $630_B$ to form tissue compression space $640_B$ (FIG. 14B). Accordingly, because the pressure exerted on the tissue segments "$T_1$", "$T_2$" by surgical fastener $630_B$ is greater than the pressure exerted on the tissue segments "$T_1$", "$T_2$" by surgical fastener $630_A$, the blood flow through the tissue surrounding surgical fastener $630_B$ will be less (more restricted) than the blood flow through the tissue surrounding surgical fastener $630_A$, thereby further facilitating hemostasis. However, because blood flow is not completely restricted through tissue compression space $640_B$, unnecessary necrosis of the stapled tissue may be prevented and/or impeded.

Figure 14C:
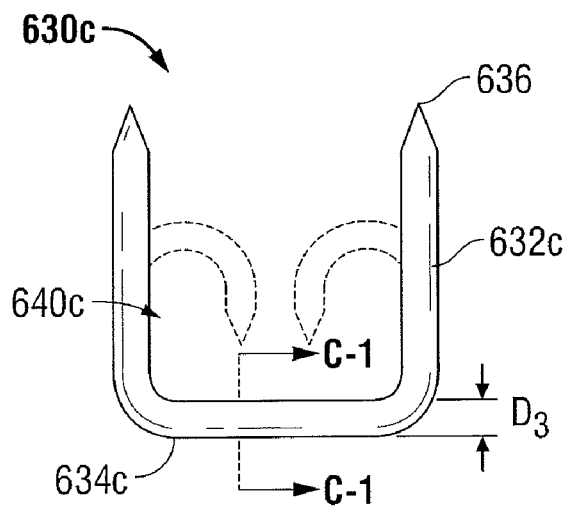
Figures 1, 14C:
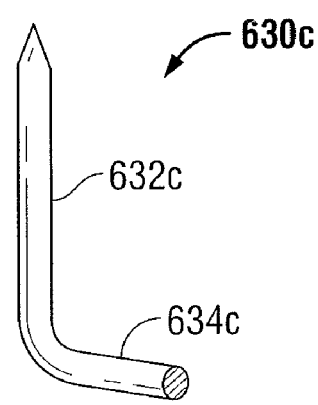

Surgical fastener $630_C$ has a diameter "$D_3$", greater than the diameter "$D_2$" of fastener $630_B$. When the surgical fastener $630_C$ is formed (phantomly shown in FIG. 14C) within tissue segments "$T_1$", "$T_2$", the backspan $634_C$ cooperates with the legs $632_C$ of the surgical fastener $630_C$ to form tissue compression space $640_C$ (FIG. 14C). The resultant compression space $640_C$ is less than the compression space $640_B$ of fastener $630_B$. Accordingly, because the pressure exerted on the tissue segments "$T_1$", "$T_2$" by surgical fastener $630_C$ is greater than the pressure exerted on the tissue segments "$T_1$", "$T_2$" by surgical fasteners $630_B$, $630_A$, the blood flow through the tissue surrounding surgical fastener $630_C$ will be less (more restricted) than the blood flow through the tissue surrounding surgical fasteners $630_B$, $630_A$, thereby further facilitating hemostasis. Because blood flow is substantially, if not completely, restricted through tissue compression space $640_C$, this results in facilitating and effectuating hemostasis.

FIG. 15 illustrates the surgical fasteners $630_C$, $630_B$, and $630_A$ loaded within the cartridge body 612 shown in FIG. 10. The surgical fasteners $630_C$, $630_B$, and $630_A$ are arranged to define a pair of inner, middle, and outer rows $628_C$, $628_B$, and $628_A$, respectively, of fastener retention slots 626 formed in the top wall 620. The pair of inner, middle, and outer rows $628_C$, $628_B$, and $628_A$, respectively, are each spaced laterally outward from the channel 622, on opposite sides thereof, such that the surgical fasteners $630_C$, $630_B$, and $630_A$ will be deployed on opposite sides of the cut-line (not shown) created in the tissue upon fastening. That is, the fasteners $630_C$ with the largest diameter provide a greater compressive force as there is a shorter distance between the inner surface of the backspan and the curve of the formed legs, and in the illustrated embodiment are provided in the inner rows closer to the cut line. The fasteners $630_B$, due to their smaller diameter, have a greater distance between the curve of the legs and the inner surface of the backspan and are provided on the outer rows where the tissue might be thicker as a result of clamping by the instrument jaws (anvil and cartridge). If a third row of fasteners $630_A$ is used in this embodiment, then the fasteners of FIG. 14A with the smallest diameter (largest compression space) would preferably be placed on the outermost row furthest from the cut line. It should be appreciated, however, that the fasteners can be placed on other rows than the foregoing. Also, while the inner, middle, and outer rows $628_C$, $628_B$, and $628_A$, respectively, are shown as including the surgical fasteners $630_C$, $630_B$, $630_A$, respectively, the present disclosure contemplates the inclusion of the surgical fasteners $630_C$, $630_B$, and $630_A$, in other rows or arrangement of any of the surgical fasteners $630_C$, $630_B$, and $630_A$, disclosed herein, either exclusively, such that only a single surgical fastener, e.g., surgical fastener 630, is present in a particular row, or in combination, such that a variety of surgical fasteners, e.g., surgical fasteners $630_C$, $630_B$, and $630_A$, are present in one or more rows.

In one particular embodiment, the outer rows $628_A$, intermediate rows $628_B$, and inner rows $628_C$ are comprised solely of surgical fasteners $630_A$, $630_B$, and $630_C$, respectively such that the flow of blood through the tissue immediately surrounding the cut-line (not shown) is substantially, if not completely, restricted by the inner row $628_C$ of surgical fasteners $630_C$, whereas the flow of blood through the tissue surrounding the intermediate and outer rows $628_B$, $628_A$ is less restricted by surgical fasteners $630_B$, $630_A$, respectively. Accordingly, the flow of blood is minimized in the tissue immediately adjacent the cut-line and is increased gradually as the lateral distance from the cut-line is also increased. Also by this arrangement, the fasteners with the smallest diameter (fasteners $630_A$), are furthest from the cut line where the tissue is generally compressed to the lesser extent and the fasteners with the larger diameter are positioned in the inner rows where the tissue is compressed to the greater extent. It should be appreciated that the diameters of the fasteners could be varied to accommodate tissue of different thicknesses and to control tissue compression by the fasteners.

Figures 1, 11A:
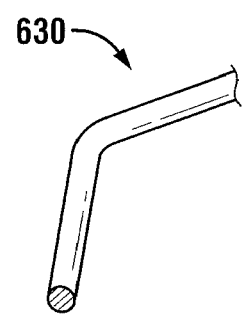
Figure 12A:
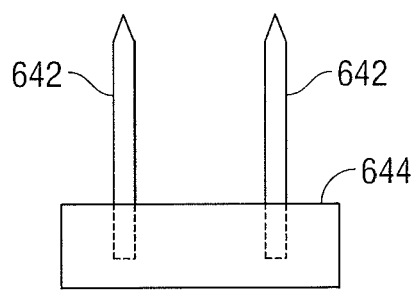
FIGS. 12A-12D illustrate different surgical fasteners that include different backspan configurations in accordance with alternate embodiments of the present disclosure.
Figure 12B:
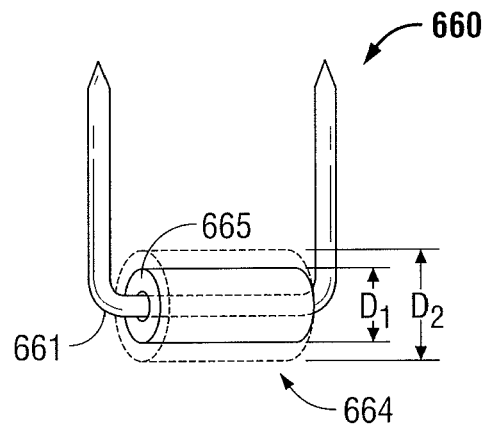
Figure 12C:
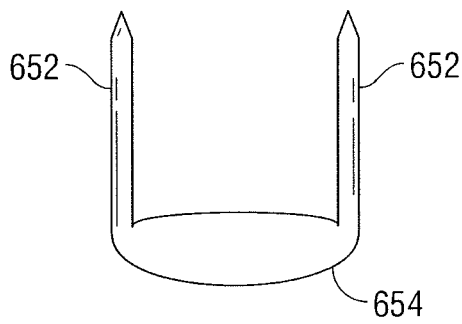
Figure 12D:
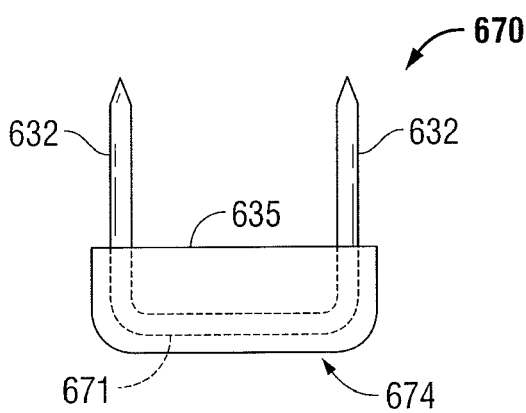

In the embodiment of FIGS. 11 and 13, the backspan and legs are shown having a uniform diameter. It should be appreciated that the diameter of the legs and backspan, or portions thereof, can vary within the fastener. Examples of varying size backspan are shown in FIGS. 12A-12B. In the embodiment of FIG. 12A, the backspan is enlarged with respect to the legs and is an integral element 644 in which the fastener legs 642 are embedded. In FIG. 12C, the backspan 654 is integral with the fastener legs 652. In the embodiments of FIGS. 12B and 12D, a separate backspan material is attached to the fastener 660, with backspan 664 of FIG. 12B including a cylindrical collar 665 encircling the backspan portion 661 of the fastener 660 and the backspan 674 of fastener 670 of FIG. 12D encompassing the backspan portion 671 of the fastener and a portion of the fastener legs 672. The backspan material of FIGS. 12B and 12D can be composed of thermoplastic overmolded to the staple leg, by way of example. Varying the thickness or height of these backspans by varying the height of the integral backspan or backspan materials can vary the compression force of the formed staple by varying the distance between the curved legs and inner portion of the backspan. This variation can be provided in addition to the varying diameters of the fastener to accommodate varying tissue thicknesses. FIG. 12B illustrates this varying backspan by showing in phantom a collar of larger diameter (D2 compared to D1) to decrease the compression area. Other backspan shapes and attachments to achieve the various compression forces are also contemplated.

From the foregoing and with reference to the various figure drawings, those skilled in the art will appreciate that certain modifications can also be made to the present disclosure without departing from the scope of the same. For example, the surgical fasteners described herein above may be formed from a variety of surgically acceptable materials including titanium, plastics, bio-absorbable materials, etc. Additionally, any of the aforementioned surgical fasteners may be treated, chemically or otherwise, prior to being loaded into cartridge 100.

It is also contemplated that the backspan e.g. backspan 634 of the surgical fasteners 630, may include one or more pockets (not explicitly shown) that are positioned to engage the legs 632 during formation of the surgical fastener 630 and configured to redirect the legs 632 such that they are coiled toward the backspan 634, as discussed in commonly owned U.S. patent application Ser. No. 11/444,664, filed Jun. 1, 2006, the entire contents of which are incorporated by reference herein.

Figure 16:
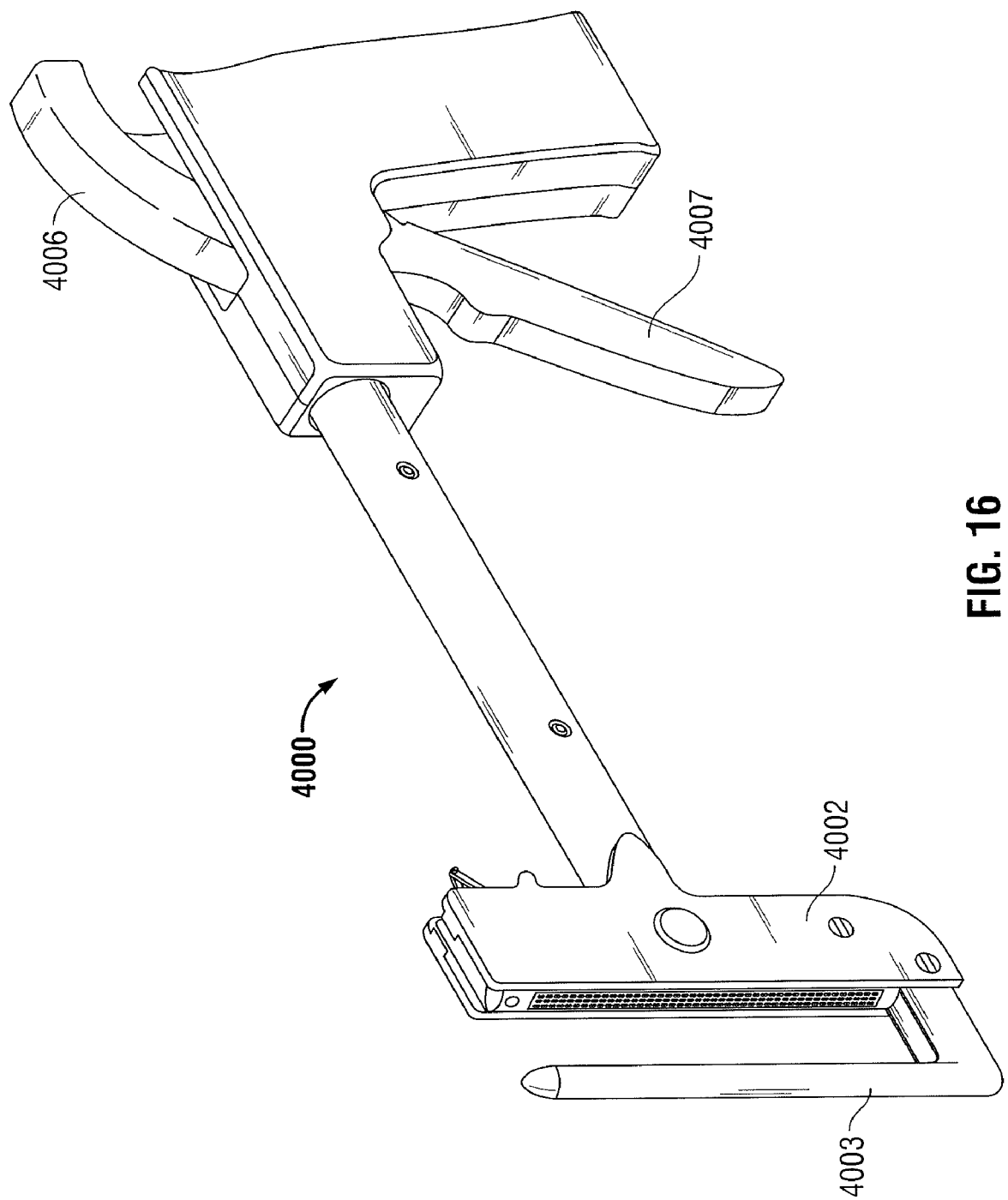
FIG. 16 illustrates another type of surgical fastener device that may employ an alternate embodiment of surgical fastener cartridge in accordance with the present disclosure.

The surgical fastening cartridge 600 may also be employed with a surgical fastener applying apparatus 4000 (FIG. 16) that is used to simultaneously deploy a plurality of surgical fasteners (surgical fasteners 630 for example), arranged in substantially linear rows transverse to a longitudinal axis of the apparatus, into either side of a target section of tissue (not explicitly shown). Here, a scalpel or other such cutting element may be used to remove the target section of tissue, or a built in knife could be provided which could be advanced upon advancement (firing) of the fasteners. The fasteners 130 would be supported within the cartridge or fastener supporting portion 4002. Approximation of the cartridge and anvil supporting portion 4003, e.g. linear movement of the fastener supporting portion 4002 toward the anvil supporting portion 4003, via movement of lever 4006 clamps tissue therebetween. The fasteners can then be advanced into the anvil pockets upon squeezing of handle 4007, providing varying compressive forces on the tissue due to the varying backspans. Further details regarding the use and function of surgical fastener applying apparatus 4000 may be obtained through reference to U.S. Pat. Nos. 7,070,083 and 5,964,394 the entire contents of which are incorporated herein by reference. In an alternate embodiment, the apparatus 4000 could include a cutting element as in the other cartridges disclosed herein. Such staplers can also include other mechanisms for approximating the anvil and cartridge and firing the fasteners. The cartridge and anvil can also be used with other apparatus for simultaneously deploying a substantially linear row of fasteners, such as U.S. Pat. No. 7,407,076, the entire contents of which is incorporated herein by reference.

As noted above, the surgical fastening cartridge 100 may also be employed with a surgical fastener applying apparatus 3000 (FIG. 3) that is used to sequentially deploy a plurality of surgical fasteners arranged in substantially linear rows substantially aligned with the longitudinal axis of the apparatus, into either side of a target section of tissue (not explicitly shown). Here, a knife is advanced with the firing of the fasteners. The fasteners 130 would be supported within the cartridge or fastener supporting portion 3002. The instrument halves 3001 and 3003 are clamped together to approximate the cartridge and anvil, and movement of firing knob 3005 sequentially fires the fasteners into contact with the anvil pockets of the anvil portion 3004, providing varying compressive forces on the tissue due to the varying backspans.

As noted above, the surgical fastening cartridge 100 may also be employed with a surgical fastener applying apparatus 2000 (FIG. 2) that is used to simultaneously deploy a plurality of surgical fasteners arranged in substantially annular rows, into either side of a target section of tissue (not explicitly shown). Here, a knife is advanced with the firing of the fasteners. The fasteners 130 would be supported within the cartridge or fastener supporting portion 2002 Approximation of the cartridge 2002 and anvil 2004, e.g. retraction of the anvil 2004 by rotation of approximation knob (wing nut) 2005 clamps tissue between the anvil 2004 and cartridge 2002. The fasteners can then be advanced into the contact with the anvil pockets by squeezing of handles 2007, providing varying compressive forces on the tissue due to the varying backspans.

Although the illustrative embodiments of the present disclosure have been described herein with reference to the accompanying drawings, the above description, disclosure, and figures should not be construed as limiting, but merely as exemplary of various embodiments.

What is claimed is:

1. A surgical fastener applying apparatus comprising:
   a cartridge body including a tissue contacting surface, the tissue contacting surface including a plurality of fastener retention slots arranged to define a plurality of rows including at least a pair of inner rows and a pair of outer rows;
   a plurality of surgical fasteners including a backspan, and a discrete member secured to the backspan, the backspan and the discrete member cooperatively defining a backspan height for each surgical fastener, the plurality of surgical fasteners arranged to define a pair of inner rows and a pair of outer rows corresponding to the pairs of inner and outer rows of retention slots, the discrete member of each of the plurality of surgical fasteners disposed in the inner rows having a first height, and the discrete member of each of the plurality of surgical fasteners disposed in the outer rows having a second height, wherein the first height is different than the second height;
   an anvil having a pair of inner rows and a pair of outer rows of depressions for forming the surgical fasteners; and
   a plurality of pushers operably associated with the plurality of surgical fasteners, and configured to eject the surgical fasteners toward a respective depression in an anvil for formation thereof such that upon formation, the plurality of surgical fasteners ejected from the inner rows provide a greater compressive force to tissue than the plurality of surgical fasteners ejected from the outer rows.

2. A surgical fastener applying apparatus according to claim 1, wherein the inner and outer rows of surgical fasteners are spaced laterally on opposite sides of a channel that is located on the tissue contacting surface and configured to accommodate longitudinal movement of a knife.

3. A surgical fastener applying apparatus according to claim 1, wherein the surgical fasteners include two legs extending from the backspan and when formed the surgical fasteners include a generally "B" shape configuration with an overall height that is measured from an outermost surface of the backspan to an outermost curve of the legs and a tissue compression space between the legs and the discrete member of the surgical fastener, wherein a tissue compression space of the plurality of surgical fasteners ejected from the inner rows is less than a tissue compression space of the plurality of surgical fasteners ejected from the outer rows.

4. A surgical fastener applying apparatus according to claim 3, wherein the discrete member is secured to the legs.

5. A surgical fastener applying apparatus according to claim 1, wherein the two legs and the backspan include the same geometrical configuration such that the cross-sectional configuration of the surgical fastener is substantially uniform.

6. A surgical fastener applying apparatus according to claim 1, wherein the two legs include a geometrical configuration that is different from a geometrical configuration of the backspan such that the cross-sectional configuration of the surgical fastener varies.

7. A surgical fastener applying apparatus according to claim 1, wherein the tissue contacting surface of the cartridge body further includes a plurality of retention slots arranged to define a pair of intermediate rows positioned between the pair of inner rows and the pair of outer rows, and the plurality of surgical fasteners are further arranged to define intermediate rows of surgical fasteners corresponding to the intermediate rows of retention slots, the plurality of surgical fasteners comprising the pair of intermediate rows each including a backspan, and a discrete member secured to the backspan, the backspan and the discrete member cooperatively defining a backspan height for each of the plurality of surgical fasteners in the intermediate rows, the discrete member of each of the plurality of surgical fasteners disposed in the intermediate rows having a third height different than at least one of the first height and the second height.

8. A surgical fastening apparatus according to claim 1, wherein the cartridge body and anvil are pivotally attached.

9. A surgical fastening apparatus according to claim 1, wherein at least one of the cartridge body and anvil is movable along a substantially linear path to move the cartridge body and anvil into approximation.

10. A surgical fastening apparatus according to claim 1, wherein the inner and outer rows of fasteners are substantially linear.

11. A surgical fastening apparatus according to claim 1, wherein the inner and outer rows of fasteners are substantially annular.

12. A surgical fastener applying apparatus according to claim 1, wherein the discrete member surrounds a portion of the backspan.

13. A surgical fastener applying apparatus according to claim 1, wherein the discrete member defines a substantially cylindrical shape.

14. A surgical fastener applying apparatus according to claim 1, wherein the discrete member defines a substantially uniform tissue contacting surface.

15. A surgical fastener applying apparatus according to claim 1, wherein the backspan and the discrete member are formed from different materials.

16. A surgical fastener applying apparatus according to claim 1, wherein the discrete members of the plurality of surgical fasteners are configured and dimensioned such that the first height is greater than the second height.

17. A surgical fastener cartridge for use with a surgical fastener applying apparatus comprising:
- a cartridge body including a plurality of fastener retention slots arranged in a plurality of rows including at least a pair of inner rows and a pair of outer rows;
- a plurality of first surgical fasteners arranged to define a pair of inner rows corresponding to the pair of inner rows of retention slots, and a plurality of second surgical fasteners arranged to define a pair of outer rows corresponding to the pair of outer rows of retention slots, each surgical fastener having a pair of legs extending from a backspan, and a discrete member secured to the backspan, the backspan and the discrete member cooperatively defining a backspan height for each surgical fastener, the discrete member of each of the plurality of first surgical fasteners having a first height, and the discrete member of each of the plurality of second surgical fasteners having a second height, wherein the first height is different than the second height; and
- a plurality of pushers operably associated with the plurality of surgical fasteners configured to eject the surgical fasteners.

18. A surgical fastener cartridge according to claim 17, wherein the cartridge body includes a tissue contacting surface having a longitudinal channel configured to accommodate longitudinal movement of a knife, the inner rows of surgical fasteners being positioned on opposite sides of the channel, and the outer rows of surgical fasteners being positioned on opposite sides of the channel, and spaced further from the channel than the inner rows.

19. A surgical fastener cartridge according to claim 18, wherein when formed the surgical fasteners include a generally "B" shaped configuration having a tissue compression spaced defined between the discrete member of the surgical fastener and a curve of the legs when formed, wherein the tissue compression space of the plurality of surgical fasteners in the inner rows is less than the tissue compression space of the plurality of surgical fasteners in the outer rows.

20. A surgical fastener cartridge according to claim 17, wherein the cartridge body further includes a plurality of retention slots arranged to define a pair of intermediate rows positioned between the pair of inner rows and the pair of outer rows, and the surgical fastener cartridge further includes a plurality of third surgical fasteners arranged to define a pair of intermediate rows corresponding to the intermediate rows of retention slots, each fastener comprising the plurality of third surgical fasteners having a pair of legs extending from a backspan, and a discrete member secured to the backspan, the backspan and the discrete member cooperatively defining a backspan height for each of the plurality of surgical fasteners in the intermediate rows, the discrete member of each of the plurality of surgical fasteners disposed in the intermediate rows having a third height different than at least one of the second height and the first height.

21. A surgical fastener applying apparatus according to claim 20, wherein the discrete members of the plurality of surgical fasteners are configured and dimensioned such that the first height is greater than the second height and the third height.

22. A surgical fastener applying apparatus according to claim 21, wherein the discrete members of the plurality of surgical fasteners are configured and dimensioned such that the second height is greater than the third height.

23. A surgical fastener cartridge according to claim 17, wherein the two legs and the backspan include the same geometrical configuration such that the cross-sectional configuration of the surgical fastener is substantially uniform.

24. A surgical fastener cartridge according to claim 17, wherein the two legs include a geometrical configuration that is different from a geometrical configuration of the backspan such that the cross-sectional configuration of the surgical fastener varies.

25. A surgical fastener cartridge of claim 24, wherein an unformed length of the legs of the plurality of surgical fasteners in the inner rows is substantially equal to an unformed length of the legs of the plurality of surgical fasteners in the outer rows.

26. A surgical fastener applying apparatus according to claim 17, wherein the discrete member surrounds a portion of the backspan.

27. A surgical fastener applying apparatus according to claim 17, wherein the discrete member defines a substantially cylindrical shape.

28. A surgical fastener applying apparatus according to claim 17, wherein the discrete member is secured to the legs.

* * * * *